US010131671B2

(12) United States Patent
Li et al.

(10) Patent No.: US 10,131,671 B2
(45) Date of Patent: Nov. 20, 2018

(54) ORGANIC COMPOUNDS

(71) Applicant: Intra-Cellular Therapies, Inc., New York, NY (US)

(72) Inventors: Peng Li, New Milford, NJ (US); Hailin Zheng, Teaneck, NJ (US); Jun Zhao, Highland Park, NJ (US); Lawrence P. Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/502,144

(22) PCT Filed: Aug. 7, 2015

(86) PCT No.: PCT/US2015/044164
§ 371 (c)(1),
(2) Date: Feb. 6, 2017

(87) PCT Pub. No.: WO2016/022893
PCT Pub. Date: Feb. 11, 2016

(65) Prior Publication Data
US 2017/0226117 A1    Aug. 10, 2017

Related U.S. Application Data

(60) Provisional application No. 62/034,567, filed on Aug. 7, 2014.

(51) Int. Cl.
C07D 487/14 (2006.01)
A61K 45/06 (2006.01)
A61K 31/519 (2006.01)

(52) U.S. Cl.
CPC .......... *C07D 487/14* (2013.01); *A61K 31/519* (2013.01); *A61K 45/06* (2013.01)

(58) Field of Classification Search
CPC ..... C07D 487/14; A61K 31/519; A61K 45/06
See application file for complete search history.

(56) References Cited

U.S. PATENT DOCUMENTS

| | | | |
|---|---|---|---|
| 4,666,908 A | 5/1987 | Hamilton | |
| 4,722,810 A | 2/1988 | Delaney et al. | |
| 4,929,641 A | 5/1990 | Haslanger et al. | |
| 5,202,328 A | 4/1993 | de Laszlo et al. | |
| 5,217,996 A | 6/1993 | Ksander | |
| 5,294,612 A | 3/1994 | Bacon et al. | |
| 5,393,755 A | 2/1995 | Neustadt et al. | |
| 5,824,683 A | 10/1998 | McKittrick et al. | |
| 5,849,770 A | 12/1998 | Head et al. | |
| 5,939,419 A | 8/1999 | Tulshian et al. | |
| 5,962,492 A | 10/1999 | Warrellow et al. | |
| 6,013,621 A | 1/2000 | Nishi et al. | |
| 6,133,273 A | 10/2000 | Gilbert et al. | |
| 6,221,335 B1 | 4/2001 | Foster | |
| 6,235,742 B1 | 5/2001 | Bell et al. | |
| 6,235,746 B1 | 5/2001 | Davis et al. | |
| 6,316,444 B1 | 11/2001 | Hunt et al. | |
| 6,334,997 B1 | 1/2002 | Foster et al. | |
| 6,423,716 B1 | 7/2002 | Matsuno et al. | |
| 6,440,710 B1 | 8/2002 | Keinan et al. | |
| 6,492,371 B2 | 12/2002 | Roylance | |
| 6,498,165 B1 | 12/2002 | Armstrong et al. | |
| 6,552,029 B1 | 4/2003 | Davis et al. | |
| 6,586,423 B2 | 7/2003 | Bilodeau et al. | |
| 6,599,908 B1 | 7/2003 | Davis et al. | |
| 6,603,008 B1 | 8/2003 | Ando et al. | |
| 6,649,608 B2 | 11/2003 | Pease et al. | |
| 6,670,368 B1 | 12/2003 | Breault et al. | |
| 6,693,099 B2 | 2/2004 | Degenhardt et al. | |
| 6,756,373 B1 | 6/2004 | Allerton et al. | |
| 6,969,719 B2 | 11/2005 | Asberom et al. | |
| 7,153,824 B2 | 12/2006 | Palmer et al. | |
| 7,157,451 B2 | 1/2007 | Atwal et al. | |
| 7,517,990 B2 | 4/2009 | Ito et al. | |
| 7,964,607 B2 | 6/2011 | Verhoest et al. | |
| 8,273,750 B2 | 9/2012 | Li et al. | |
| 8,273,751 B2 | 9/2012 | Li et al. | |
| 8,513,244 B2 | 8/2013 | Gendron et al. | |
| 8,536,159 B2 | 9/2013 | Li et al. | |
| 8,633,180 B2 | 1/2014 | Li et al. | |

(Continued)

FOREIGN PATENT DOCUMENTS

| | | |
|---|---|---|
| DE | 19931206 A1 | 1/2001 |
| DE | 10 2005 042 877 A1 | 3/2007 |
| EP | 0 063 381 A1 | 10/1982 |

(Continued)

OTHER PUBLICATIONS

Adamo et aL, "Molecular targets for PDE inhibitor-mediated improvement of cardiac dysfunction in the mdx mouse?" BMC Pharmacology, 2011, 11(Suppl 1):O20 (Abstract Only).

Ahn, H. et al., "Potent Tetracyclic Guanine Inhibitors of PDE1 and PDE5 Cyclic Guanosine Monophosphate Phosphodiesterases with Oral Antihypertensive Activity," Journal of Medicinal Chemistry, 1997, 40 (14), 2196-2210.

Al-Afaleq, E. et al., "Heterocyclic o-Aminonitriles: Preparation of Pyrazolo[3,4-d]-pyrimidines with Modification of the Substituents at the 1-Position," Molecules, 2001, 6, 621-638.

"Anxiety," [retrieved on May 14, 2008]. Retrieved online via Internet, URL: http://www.nlm.nih.gov/medlineplus/anxiety.html, 5 pages.

(Continued)

*Primary Examiner* — Erich A Leeser
(74) *Attorney, Agent, or Firm* — Hoxie & Associates LLC

(57) ABSTRACT

The invention relates to novel inhibitors of phosphodiesterase 1 (PDE1), useful for the treatment of diseases or disorders characterized by disruption of or damage to certain cGMP/PKG mediated pathways (e.g., in cardiac tissue). The invention further relates to pharmaceutical composition comprising the same and methods of treatment of cardiovascular disease and related disorders, e.g., congestive heart disease, atherosclerosis, myocardial infarction, and stroke.

38 Claims, No Drawings

(56) References Cited

U.S. PATENT DOCUMENTS

| | | |
|---|---|---|
| 8,664,207 B2 | 3/2014 | Li et al. |
| 8,697,710 B2 | 4/2014 | Li et al. |
| 8,829,008 B2 | 9/2014 | Li et al. |
| 8,846,693 B2 | 9/2014 | Li et al. |
| 8,858,911 B2 | 10/2014 | Li et al. |
| 8,859,564 B2 | 10/2014 | Li et al. |
| 8,927,556 B2 | 1/2015 | Li et al. |
| 9,000,001 B2 | 4/2015 | Li et al. |
| 9,006,258 B2 | 4/2015 | Fienberg et al. |
| 9,073,936 B2 | 7/2015 | Li et al. |
| 9,157,906 B2 | 10/2015 | Greengard et al. |
| 9,198,924 B2 | 12/2015 | Mates et al. |
| 9,255,099 B2 | 2/2016 | Li et al. |
| 9,371,327 B2 | 6/2016 | Li et al. |
| 9,403,836 B2 | 8/2016 | Li |
| 9,434,730 B2 | 9/2016 | Li et al. |
| 9,468,637 B2 | 10/2016 | Fienberg et al. |
| 9,469,647 B2 | 10/2016 | Li et al. |
| 9,487,527 B2 | 11/2016 | Li et al. |
| 9,763,948 B2 | 9/2017 | Li et al. |
| 9,801,882 B2 | 10/2017 | Wennogle et al. |
| 9,884,872 B2 | 2/2018 | Li et al. |
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2003/0211040 A1 | 11/2003 | Greengard et al. |
| 2004/0087517 A1 | 5/2004 | Burnet et al. |
| 2004/0259792 A1 | 12/2004 | Palmer et al. |
| 2005/0075795 A1 | 4/2005 | Pandit |
| 2005/0113379 A1 | 5/2005 | Ge et al. |
| 2006/0041014 A1 | 2/2006 | Naylor et al. |
| 2006/0252790 A1 | 11/2006 | Allen et al. |
| 2007/0082929 A1 | 4/2007 | Gant et al. |
| 2007/0197695 A1 | 8/2007 | Potyen et al. |
| 2008/0096870 A1 | 4/2008 | Martynyuk et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0273754 A1 | 10/2010 | Li |
| 2010/0323997 A1 | 12/2010 | Fienberg et al. |
| 2011/0190373 A1 | 8/2011 | Yan et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1* | 3/2012 | Fienberg .............. A61K 31/495 514/262.1 |
| 2012/0070443 A1 | 3/2012 | Movsesian |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li |
| 2012/0238589 A1 | 9/2012 | Li |
| 2013/0018063 A1 | 1/2013 | Li et al. |
| 2013/0085123 A1 | 4/2013 | Li et al. |
| 2013/0149309 A1 | 6/2013 | Greengard et al. |
| 2013/0239234 A1 | 9/2013 | Greengard et al. |
| 2013/0324565 A1 | 12/2013 | Li et al. |
| 2013/0330365 A1 | 12/2013 | Hughes et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2014/0275131 A1 | 9/2014 | Li et al. |
| 2014/0315868 A1 | 10/2014 | Li et al. |
| 2014/0357606 A1 | 12/2014 | Li et al. |
| 2015/0038474 A1 | 2/2015 | Li et al. |
| 2015/0072965 A1 | 3/2015 | Li et al. |
| 2015/0080357 A1 | 3/2015 | Li et al. |
| 2015/0119370 A1 | 4/2015 | Li et al. |
| 2015/0139903 A1 | 5/2015 | Li et al. |
| 2015/0197524 A1 | 7/2015 | Li et al. |
| 2015/0197528 A1 | 7/2015 | Li et al. |
| 2015/0353556 A1 | 12/2015 | Li et al. |
| 2015/0374699 A1 | 12/2015 | Wennogle et al. |
| 2016/0031895 A1 | 2/2016 | Li et al. |
| 2016/0038494 A1 | 2/2016 | Wennogle et al. |
| 2016/0039835 A1 | 2/2016 | Li et al. |
| 2016/0083390 A1 | 3/2016 | Li et al. |
| 2017/0197974 A1 | 7/2017 | Li et al. |
| 2018/0000825 A1 | 1/2018 | Wennogle et al. |

FOREIGN PATENT DOCUMENTS

| | | |
|---|---|---|
| EP | 0 095 289 A2 | 11/1983 |
| EP | 0136883 A2 | 4/1985 |
| EP | 0 201 188 A2 | 12/1986 |
| EP | A 0274234 A2 | 7/1988 |
| EP | 0358398 A1 | 3/1990 |
| EP | 0509442 A1 | 10/1992 |
| EP | 0519738 A1 | 12/1992 |
| EP | 0599444 A1 | 6/1994 |
| EP | 0 636 626 A1 | 2/1995 |
| EP | 0690070 A1 | 1/1996 |
| EP | 0733642 A1 | 9/1996 |
| EP | 0830863 A1 | 3/1998 |
| EP | 0 911 333 A1 | 4/1999 |
| EP | 1097719 A1 | 5/2001 |
| JP | 53031694 A | 3/1978 |
| KR | 10-1991-0006866 | 9/1991 |
| WO | WO 91/09840 | 7/1991 |
| WO | WO 91/19717 | 12/1991 |
| WO | WO 93/09101 | 5/1993 |
| WO | WO 94/15908 | 7/1994 |
| WO | WO 94/19351 | 9/1994 |
| WO | WO 96/14293 | 5/1996 |
| WO | WO 98/46606 | 10/1998 |
| WO | WO 98/52568 | 11/1998 |
| WO | WO 01/27113 | 4/2001 |
| WO | WO 02/074312 | 9/2002 |
| WO | WO 03/002567 | 1/2003 |
| WO | WO 03/020702 | 3/2003 |
| WO | WO 03/020724 | 3/2003 |
| WO | WO 03/042216 | 5/2003 |
| WO | WO 2006/133261 | 12/2006 |
| WO | WO 2007/143568 | 12/2007 |
| WO | WO 2007/143705 | 12/2007 |
| WO | WO 2008/063505 | 5/2008 |
| WO | WO 2008/070095 | 6/2008 |
| WO | WO 2009/073210 | 6/2009 |
| WO | WO 2009/075784 | 6/2009 |
| WO | WO 2009/137465 | 11/2009 |
| WO | WO 2010/065147 | 6/2010 |
| WO | WO 2010/065148 | 6/2010 |
| WO | WO 2010/065149 | 6/2010 |
| WO | WO 2010/065151 | 6/2010 |
| WO | WO 2010/065152 | 6/2010 |
| WO | WO 2010/065153 | 6/2010 |
| WO | WO 2010/065617 | 6/2010 |
| WO | WO 2010/098839 | 9/2010 |
| WO | WO 2011/016861 | 2/2011 |
| WO | WO 2011/043816 | 4/2011 |
| WO | WO 2011/133224 | 10/2011 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/171016 | 12/2012 |
| WO | WO 2013/192556 | 12/2013 |
| WO | WO 2014/127331 | 8/2014 |
| WO | WO 2014/151409 | 9/2014 |

OTHER PUBLICATIONS

Aswar, M. et al., "Anti-Cataleptic Activity of Various Extracts of *Ocimum sanctum*," International Journal of Pharmaceutical Research and Development, 2010, 2 (6), 7 pages.

(56) References Cited

OTHER PUBLICATIONS

"Autism," [retrieved on May 14, 2008]. Retrieved online via Internet, URL: http://www.nlm.nih.gov/medlineplus/autism.html, 6 pages.

Banker, Gilbert S. et al., Eds., Modern Pharmaceutics, Third Edition, Marcel Dekker Inc., New York, 1996.

Bastia, E. et al., "Effect of $A_1$ and $A_{2A}$ Adenosine Receptor Ligands in Mouse Acute Models of Pain," Neuroscience Letters, 2002, 328, 241-244.

Bender, A. et al., "Cyclic Nucleotide Phosphodiesterases: Molecular Regulation to Clinical Use," Pharmacological Reviews, 2006, 58 (3), 488-520.

Blokland, A. et al., "PDE Inhibition and Cognition Enhancement," 2012, 22 (4), 349-354 (abstract only).

Boyd, K. et al., "Dopamine Receptor Signaling and Current and Future Antipsychotic Drugs" in Current Antipsychotics, Handbook of Experimental Pharmacology, 212, Gross, G. et al., Eds., doi:10.1007/978-3-642-25761-2_3, Springer-Verlag, Berlin, 2012, pp. 53-86.

Burnouf, C. et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors," Journal of Medicinal Chemistry, 2000, 43 (25), 4850-4867.

Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.

Chebib, M. et al., "1-Phenylpyrazolo[3,4-d]pyrimidines; Structure-Activity Relationships for C6 Substituents at $A_1$ and $A_{2A}$ Adenosine Receptors," Bioorganic & Medicinal Chemistry, 2000, 8, 2581-2590.

Chen, M. et al., "Effects of Bimatoprost 0.03% on Ocular Hemodynamics in Normal Tension Glaucoma," Journal of Ocular Pharmacology and Therapeutics, 2006, 22 (3), 188-193.

Chermat, R. et al., "Adaptation of the Tail Suspension Test to the Rat," Journal de Pharmacologie (Paris), 1986, 17 (3), 348-350.

Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.

Dewald, H. et aL, "Synthesis and Potential Antipsychotic Activity of 1H-Imidazo[1,2-c]pyrazolo[3,4-e]pyrimidines," Journal of Medicinal Chemistry, 1988, 31, 454-461.

Ehrman, L. et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, 2006, 5 (7), 540-551.

English Abstract of DE19931206, date of publication of application: Jan. 11, 2001, 2 pages, obtained through E-Spacenet, date accessed: Oct. 6, 2017.

English Abstract of DE102005042877, date of publication of application: Mar. 22, 2007, 1 page, obtained through E-Spacenet, date accessed: Nov. 15, 2016.

Ennaceur, A. et al., "A New One-Trial Test for Neurobiological Studies of Memory in Rats. 1:Behavioral Data," Behavioural Brain Research, 1998, 31, 47-59.

Fienberg, A. et al., "DARPP-32: Regulator of the Efficacy of Dopaminergic Neurotransmission," Science, 1998, 281, 838-842.

Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.

Gelbin, M. et al., "Ketene-S,N-acetals as Synthons for Heterocycles, New Synthesis of Pyrimidinones," Journal Für Praktische Chemie, 1987, 329 (5), 753-766.

Ghorab, M.M. et al, Synthesis, anticancer and radioprotective activities of some new pyrazolo[3,4-d]pyrimidines containing amino acid moieties, Arzneimittel Forschung, 2009, vol. 59, No. 2, pp. 96-103.

Giachini et al., "CHBPR: Decreased cGMP level contributes to increased contraction in arteries from hypertensive rats: role of PDE1," Hypertension, 2011, 57(3), 655-663.

Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.

Greengard, P. et al., "Beyond the Dopamine Receptor: The DARPP-32/Protein Phosphatase-1 Cascade," Neuron, 1999, 23, 435-447.

Gulyas, B. et al., "PET studies on the brain uptake and regional distribution of [$^{11}$C]vinpocetine in human subjects," Acta Neurologica Scandinavica, 2002, 106, pp. 325-332.

Hall et al., "Autoradiographic evaluation of [11C]vinpocetine Binding in the Human Postmortem Brain," Acta Biologica Hungarica, 2002, 53(1-2), 59-66.

Han, P. et al., "The Calcium/Calmodulin-dependent Phosphodiesterase PDE1C Down-regulates Glucose-induced Insulin Secretion," The Journal of Biological Chemistry, 1999, 274 (32), 22337-22344.

Hulley, P. et aL, "Cyclic AMP Promotes the Survival of Dopaminergic Neurons in vitro and Protects Them from the Toxic Effects of MPP$^+$," Journal of Neural Transmission [Supplemental], 1995, 46, 217-228.

International Search Report for International Application No. PCT/US2014/016741, prepared by the International Searching Authority, dated May 14, 2014, 3 pages.

Japanese Patent Office, Patent Abstracts of Japan, Abstract for JP 53031694 A, Date of publication of application Mar. 25, 1978, 1 page.

Jiang, M. et aL, "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," Journal of Organic Chemistry, 2005, 70, 2824-2827.

Kakkar, R. et al., "Inhibition of Bovine Brain Calmodulin-Dependent Cyclic Nucleotide Phosphodiesterase Isozymes by Deprenyl," Life Sciences, 1996, 59 (21), 337-341.

Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.

Kakkar, R. et al. "Calmodulin-dependent Cyclic Nucleotide Phosphodiesterase (PDE1)," CMLS Cellular and Molecular Life Sciences, 1999, 55 (8-9), 1164-1186.

Kakkar et al., "Calmodulin-dependent cyclic nucleotide phosphodiesterase in an experimental rat model of cardiac ischemia-reperfusion." Can J Physiol Pharmacol, 2002, 80(1), 59-66 (Abstract Only).

Kim et al., "Upregulation of Phosphodiesterase 1A1 Expression Is Associated With the Development of Nitrate Tolerance." Circulation, 2001, 104(19), 2338-43.

Klaissle, P. et al., "Physical Activity and Environmental Enrichment Regulate the Generation of Neural Precursors in the Adult Mouse Substantia Nigra in a Dopamine-dependent Manner," BMC Neuroscience, 2012, 13, 132, doi:10.1186/1471-2202-13-132, 15 pages.

Kleppisch, T., "Phosphodiesterases in the Central Nervous System" in cGMP: Generators, Effectors and Therapuetic Implications, Handbook of Experimental Pharmacology, 191, Schmidt, H. et al., Eds., Springer-Verlag, Berlin, 2009, pp. 71-92.

Laddha, S. et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, 2009, 17 (19), 6796-6802.

Lourenco et al, "Characterization of R-[$^{11}$C]rolipram for PET imaging of phosphodiesterase-4; in vivo binding, metabolism, and dosimetry studies in rats," Nuclear Medicine and Biology, 2001, 28, pp. 347-358.

Lundqvist, T. et al., "Exploitation of Structural and Regulatory Diversity in Glutamate Racemases," Nature, 2007, 447, 817-822.

Mani, S. et aL, "Requirement for DARPP-32 in Progesterone Facilitated Sexual Receptivity in Female Rats and Mice," Science, 2000, 287, 1053-1056.

(56) References Cited

OTHER PUBLICATIONS

Medina, A., "Therapeutic Utility of Phosphodiesterase Type 1 Inhibitors in Neurological Conditions," Frontiers in Neuroscience, 2011, 5, 21, 6 pages.
Miller et al., "Role of $Ca^{2+}$/calmodulin-stimulated cyclic nucleotide phosphodiesterase 1 in mediating cardiomyocyte hypertrophy." Circ Res 2009, 105(10), 956-64.
Miller et al., "Cyclic nucleotide phosphodiesterase 1A: a key regulator of cardiac fibroblast activation and extracellular matrix remodeling in the heart," Basic Res Cardiol., 2011, 106(6), 1023-1039.
Mokni et al., "Concerted Regulation of cGMP and cAMP Phosphodiesterases in Early Cardiac Hypertrophy Induced by Angiotensin II," PLoS One., 2010 5(12):e14227, 15 pages.
Murray, "Expression and activity of cAMP phosphodiesterase isoforms in pulmonary artery smooth muscle cells from patients with pulmonary hypertension: role for PDE1," Am. J. Phusiol Lng Cell Mol Phsiol, 2006, 292: L294-303.
Murray, T. et al., "LY503430, A Novel α-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.
Noguchi, M. et al., "A Facile Preparation of 7-(Substituted Amino-)-6H-pyrrolo[3,4-d]-pyrimidine Derivatives," Bulletin of the Chemical Society of Japan, 1989, 62 (9), 3043-3045.
Pardo, C. et al., "Synthesis of 1-(p-Nitrobenzyl)Azoles and 1-(p-Nitrobenzyl)Benzazoles," OPPI Briefs, 2000, 32 (4), 385-390.
Park, E, et al., "Traumatic Brain Injury: Can the Consequences Be Stopped?" CMAJ, 2008, 178 (9), 1163-1170.
Patani et al., "Bioisosterism: A Rational Approach in Drug Design," Chem. Rev. 1996, 96, 3147-3176.
Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.
Porsolt, R. et al., "Depression: A New Animal Model Sensitive to Antidepressant Treatments," Nature, 1977, 266, 730-732.
Poulsen, S. et al., "High-Pressure Synthesis of Enantiomerically Pure C-6 Substituted Pyrazolo[3,4-d]pyrimidines," Biorganic & Medicinal Chemistry Letters, 2001, 11, 191-193.
Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.
Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.
Rybalkin, S. et al., "Cyclic GMP Phosphodiesterases and Regulation of Smooth Muscle Function," Circulation Research, 2003, 93, 280-291.
Rybalkin et al., "Cyclic Nucleotide Phosphodiesterase 1C Promotes Human Arterial Smooth Muscle Cell Proliferation," Circulation Research, 2002, 90(2), 151-7.
Schmidt, C., "Phosphodiesterase Inhibitors as Potential Cognition Enhancing Agents," Current Topics in Medicinal Chemistry, 2010, 10 (2), 222-230.
Sharma, R. et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) Is a Pharmacological Target of Differentiation-Inducing Factor-1, an Antitumor Agent Isolated from *Dictyostelium*," Cancer Research, 2004, 64, 2568-2571.
Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.
Silva et al., "Advances in Prodrug Design," Mini-Reviews in Medicinal Chemistry, 2005, 5, 893-914.
Takimoto, E., "Controlling Myocyte cGMP: Phosphodiesterase 1 Joins the Fray," Circ Res., 2009, 105(10), 931-933.
Turko, I. et al., "Inhibition of Cyclic GMP-Binding Cyclic GMP-Specific Phosphodiesterase (Type 5) by Sildenafil and Related Compounds," Molecular Pharmacology, 1999, 56, 124-130.
Ungerstedt, U. et al., "Quantitative Recording of Rotational Behavior in Rats After 6-Hydroxy-dopamine Lesions of the Nigrostriatal Dopamine System," Brain Research, 1970, 24, 485-493.
Ungerstedt, U., "Stereotaxic Mapping of the Monoamine Pathways in the Rat Brain*," Acta Physiologica Scandinavica, Supplementum 367, 1971, 1-48.
Vas, A. et al. "Clinical and non-clinical investigations using positron emission tomography, near infrared spectroscopy and transcranial Doppler methods on the neuroprotective drug vinpocetine: A summary of evidences," Journal of the Neurological Sciences, 2002, pp. 259-262.
Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.
Wallis et al., "Tissue Distribution of Phosphodiesterase Families and the Effects of Sildenafil on Tissue Cyclic Nucleotides, Platelet Function, and the Contractile Responses of Trabeculae Carneae and Aortic Rings In Vitro." Am J Cardiol., 1999, 83(5A), 3C-12C.
Wermuth, CG, ed., "Molecular Variations based on isosteric replacements," The Practice of Chemistry, Technomics, Inc., Aug. 1998, vol. 1, Section 13, pp. 235-271, Japanese Translated Version.
Wolff, Burger's Medicinal Chemistry and Drug Discovery, Fifth Edition, vol. I: Principles and Practice, John Wiley & Sons, New York, 1995, 975-977.
Xia et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.
Youdim et al., "The Path from Anti Parkinson Drug Selegiline and Rasagiline to Multi-functional Neuroprotective Anti Alzheimer Drugs Ladostigil and M30," Current Alzheimer Research, 2006, 3, 541-550.
Zhang et al., "Phosphodiesterases and cardiac cGMP: evolving roles and controversies," Trends in Pharmacological Sciences, 2011, 32(6), 360-365.
International Search Report for International Application No. PCT/US2015/044164, prepared by the International Search Authority, dated Oct. 29, 2015, 3 pages.
Bender et al., "Selective up-regulation of PDE1B2 upon monocyte-to-macrophage differentiation," PNAS, 2005, 102(2):497-502.
English Abstract of EP0063381, date of publication of application: Oct. 27, 1982, 1 page, obtained through E-Spacenet, date accessed: Mar. 20, 2018.
Evgenov et al., "Inhibition of phosphodiesterase 1 augments the pulmonary vasodilator response to inhaled nitric oxide in awake lambs with acute pulmonary hypertension," Am J Physiol Lung Cell Mol Physiol, 2006, 290:L723-L729.
Schermuly et al., "Phosphodiesterase 1 Upregulation in Pulmonary Arterial Hypertension," Circulation, 2007, 115:2331-2339.
Snyder, G.L. et al., "Preclinical Profile of ITI-214, an Inhibitor of Phosphodiesterase 1, for Enhancement of Memory Performance in Rats," Psychopharmacology, 2016, 233, 3113-3124, DOI: 10.1007/s00213-016-4346-2.
Willerson et al., "Inflammation as a Cardiovascular Risk Factor," Circulation, 2004, 109: II-2-II-10.

\* cited by examiner

ORGANIC COMPOUNDS

CROSS-REFERENCE TO RELATED APPLICATIONS

This application is a U.S. National Stage application of PCT/US2015/044164, filed on Aug. 7, 2015, which claims priority to and the benefit of U.S. Provisional Application No. 62/034,567, filed on Aug. 7, 2014, the contents of each which are hereby incorporated by reference in their entireties.

FIELD OF THE INVENTION

The invention relates to novel inhibitors of phosphodiesterase 1 (PDE1) useful for the treatment of diseases or disorders characterized by disruption of or damage to certain cGMP/PKG mediated pathways (e.g., in cardiac tissue or in vascular smooth muscle). The invention further relates to pharmaceutical composition comprising the same and methods of treatment of cardiovascular disease and related disorders, e.g., congestive heart disease, atherosclerosis, myocardial infarction, and stroke.

BACKGROUND OF THE INVENTION

Heart disease is a chronic and progressive illness that kills more than 2.4 million Americans each year. There are approximately 500,000 new cases of heart failure per year, with an estimated 5 million patients in the United States alone having this disease. Early intervention is likely to be most effective in preserving cardiac function. It would be most desirable to prevent as well to reverse the morphological, cellular, and molecular remodeling that is associated with heart disease. Some of the most important indicators of cardiac risk are age, hereditary factors, weight, smoking, blood pressure, exercise history, and diabetes. Other indicators of cardiac risk include the subject's lipid profile, which is typically assayed using a blood test, or any other biomarker associated with heart disease or hypertension. Other methods for assaying cardiac risk include, but are not limited to, an EKG stress test, thallium stress test, EKG, computed tomography scan, echocardiogram, magnetic resonance imaging study, non-invasive and invasive arteriogram, and cardiac catheterization.

Pulmonary hypertension (PH or PHT) is an increase in blood pressure in the pulmonary artery, pulmonary vein, and/or pulmonary capillaries. It is a very serious condition, potentially leading to shortness of breath, dizziness, fainting, decreased exercise tolerance, heart failure, pulmonary edema, and death. It can be one of five different groups, classified by the World Health Organization in categories described below.

WHO Group I—Pulmonary arterial hypertension (PAH):
  a. Idiopathic (IPAH)
  b. Familial (FPAH)
  c. Associated with other diseases (APAH): collagen vascular disease (e.g. scleroderma), congenital shunts between the systemic and pulmonary circulation, portal hypertension, HIV infection, drugs, toxins, or other diseases or disorder.
  d. Associated with venous or capillary disease.

Pulmonary arterial hypertension involves the vasoconstriction or tightening of blood vessels connected to and within the lungs. This makes it harder for the heart to pump blood through the lungs, much as it is harder to make water flow through a narrow pipe as opposed to a wide one. Over time, the affected blood vessels become both stiffer and thicker, in a process known as fibrosis. This further increases the blood pressure within the lungs and impairs their blood flow. In addition, the increased workload of the heart causes thickening and enlargement of the right ventricle, making the heart less able to pump blood through the lungs, causing right heart failure. As the blood flowing through the lungs decreases, the left side of the heart receives less blood. This blood may also carry less oxygen than normal. Therefore, it becomes more and more difficult for the left side of the heart to pump to supply sufficient oxygen to the rest of the body, especially during physical activity.

WHO Group II—Pulmonary hypertension associated with left heart disease:
  a. Atrial or ventricular disease
  b. Valvular disease (e.g. mitral stenosis)

In pulmonary hypertension WHO Group II, there may not be any obstruction to blood flow in the lungs. Instead, the left heart fails to pump blood efficiently out of the heart into the body, leading to pooling of blood in veins leading from the lungs to the left heart (congestive heart failure or CHF). This causes pulmonary edema and pleural effusions. The fluid build-up and damage to the lungs may also lead to hypoxia and consequent vasoconstriction of the pulmonary arteries, so that the pathology may come to resemble that of Group I or III.

WHO Group III—Pulmonary hypertension associated with lung diseases and/or hypoxemia:
  a. Chronic obstructive pulmonary disease (COPD), interstitial lung disease (ILD)
  b. Sleep-disordered breathing, alveolar hypoventilation
  c. Chronic exposure to high altitude
  d. Developmental lung abnormalities In hypoxic pulmonary hypertension (WHO Group III), the low levels of oxygen may cause vasoconstriction or tightening of pulmonary arteries. This leads to a similar pathophysiology as pulmonary arterial hypertension.

WHO Group IV—Pulmonary hypertension due to chronic thrombotic and/or embolic disease:
  a. Pulmonary embolism in the proximal or distal pulmonary arteries
  b. Embolization of other matter, such as tumor cells or parasites In chronic thromboembolic pulmonary hypertension (WHO Group IV), the blood vessels are blocked or narrowed with blood clots. Again, this leads to a similar pathophysiology as pulmonary arterial hypertension.

WHO Group V—Miscellaneous

Treatment of pulmonary hypertension has proven very difficult. Antihypertensive drugs that work by dilating the peripheral arteries are frequently ineffective on the pulmonary vasculature. For example, calcium channel blockers are effective in only about 5% of patients with IPAH. Left ventricular function can often be improved by the use of diuretics, beta blockers, ACE inhibitors, etc., or by repair/replacement of the mitral valve or aortic valve. Where there is pulmonary arterial hypertension, treatment is more challenging, and may include lifestyle changes, digoxin, diuretics, oral anticoagulants, and oxygen therapy are conventional, but not highly effective. Newer drugs targeting the pulmonary arteries, include endothelin receptor antagonists (e.g., bosentan, sitaxentan, ambrisentan), phosphodiesterase type 5 inhibitors (e.g., sildenafil, tadalafil), prostacyclin derivatives (e.g., epoprostenol, treprostinil, iloprost, beraprost), and soluble guanylate cyclase (sGC) activators (e.g., cinaciguat and riociguat). Surgical approaches to PAH include atrial septostomy to create a communication between the right and left atria, thereby relieving pressure on the right side of the heart, but at the cost of lower oxygen levels in blood (hypoxia); lung transplantation; and pulmonary thromboendarterectomy (PTE) to remove large clots along with the lining of the pulmonary artery. Heart failure and acute myocardial infarction are common and serious conditions frequently associated with thrombosis and/or plaque build-up in the coronary arteries.

Cardiovascular disease or dysfunction may also be associated with diseases or disorders typically thought of as affecting skeletal muscle. One such disease is Duchenne muscular dystrophy (DMD), which is a disorder that primarily affects skeletal muscle development but can also result in cardiac dysfunction and cardiomyopathy. DMD is a recessive X-linked form of muscular dystrophy, affecting around 1 in 3,600 boys, which results in muscle degeneration and eventual death. The disorder is caused by a mutation in the dystrophin gene, located on the human X chromosome, which codes for the protein dystrophin, an important structural component within muscle tissue that provides structural stability to the dystroglycan complex (DGC) of the cell membrane. While both sexes can carry the mutation, females rarely exhibit signs of the disease.

Patients with DMD either lack expression of the protein dystrophin or express inappropriately spliced dystrophin, as a result of mutations in the X-linked dystrophin gene. Additionally, the loss of dystrophin leads to severe skeletal muscle pathologies as well as cardiomyopathy, which manifests as congestive heart failure and arrhythmias. The absence of a functional dystrophin protein is believed to lead to reduced expression and mis-localization of dystrophin-associated proteins including Neuronal Nitric Oxide (NO) Synthase (nNOS). Disruption of nNOS signaling may result in muscle fatigue and unopposed sympathetic vasoconstriction during exercise, thereby increasing contraction-induced damage in dystrophin-deficient muscles. The loss of normal nNOS signaling during exercise is central to the vascular dysfunction proposed to be an important pathogenic mechanism in DMD. Eventual loss of cardiac function often leads to heart failure in DMD patients.

Currently, there is a largely unmet need for an effective way of treating cardiovascular disease and disorders (e.g. congestive heart disease), and diseases and disorders which may result in cardiac dysfunction or cardiomyopathy (e.g., Duchenne Muscular Dystrophy). Improved therapeutic compounds, compositions and methods for the treatment of cardiac conditions and dysfunction are urgently required.

Eleven families of phosphodiesterases (PDEs) have been identified but only PDEs in Family I, the $Ca^{2+}$-calmodulin-dependent phosphodiesterases (CaM-PDEs), which are activated by the $Ca^{2+}$-calmodulin and have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it is also detected in the heart, is present in neutrophils and has been shown to be involved in inflammatory responses of this cell. PDE1C is expressed in olfactory epithelium, cerebellar granule cells, striatum, heart, and vascular smooth muscle. PDE1C is a major phosphodiesterase in the human cardiac myocyte.

Of all of the PDE families, the major PDE activity in the human cardiac ventricle is PDE1. Generally, there is a high abundance of PDE1 isoforms in: cardiac myocytes, vascular endothelial cells, vascular smooth muscle cells, fibroblasts and motor neurons. Up-regulation of phosphodiesterase 1A expression is associated with the development of nitrate tolerance. Kim et al., *Circulation* 104(19:2338-2343 (2001). Cyclic nucleotide phosphodiesterase 1C promotes human arterial smooth muscle cell proliferation. Rybalkin et al., *Circ. Res.* 90(2):151-157 (2002). The cardiac ischemia-reperfusion rat model also shows an increase in PDE1 activity. Kakkar et al., *can. J. Physiol. Pharmacol.* 80(1): 59-66 (2002). $Ca^{2+}$/CaM-stimulated PDE1, particularly PDE1A has been shown to be involved in regulating pathological cardiomyocyte hypertrophy. Millet et al., *Circ. Res.* 105(10):956-964 (2009). Early cardiac hypertrophy induced by angiotensin II is accompanied by 140% increases in PDE1A in a rat model of heart failure. Mokni et al., *Plos. One.* 5(12):e14227 (2010). Inhibition of phosphodiesterase 1 augments the pulmonary vasodilator response to inhaled nitric oxide in awake lambs with acute pulmonary hypertension. Evgenov et al., *Am. J. Physiol. Lung Cell. Mol. Physiol.* 290(4):L723-L729 (2006). Strong upregulation of the PDE1 family in pulmonary artery smooth muscle cells is also noted in human idiopathic PAH lungs and lungs from animal models of PAH. Schermuly et al., *Circulation* 115 (17)2331-2339 (2007). PDE1A and 1C, found in fibroblasts, are known to be up-regulated in the transition to the "synthetic phenotype", which is connected to the invasion of diseased heart tissue by pro-inflammatory cells that will deposit extracellular matrix. PDE1B2, which is present in neutrophils, is up-regulated during the process of differentiation of macrophages. Bender et al., *PNAS* 102(2):497-502 (2005). The differentiation of monocytes to macrophage, in turn, is involved in the inflammatory component of heart disease, particularly atherothrombosis, the underlying cause of approximately 80% of all sudden cardiac death. Willerson et al., *Circulation* 109:II-2-II-10 (2004).

Cyclic nucleotide phosphodiesterases downregulate intracellular cAMP and cGMP signaling by hydrolyzing these cyclic nucleotides to their respective 5'-monophosphates (5'AMP and 5'GMP). cGMP is a central intracellular second-messenger regulating numerous cellular functions. In the cardiac myocyte, cGMP mediates the effects of nitric oxide and atrial natriuretic peptide, whereas its counterpart, cAMP, mediates catecholamine signaling. Each cyclic nucleotide has a corresponding primary targeted protein kinase, PKA for cAMP, and PKG for cGMP. PKA stimulation is associated with enhanced contractility and can stimulate growth, whereas PKG acts as a brake in the heart, capable of countering cAMP-PKA-contractile stimulation and inhibiting hypertrophy. Importantly, the duration and magnitude of these signaling cascades are determined not only by generation of cyclic nucleotides, but also by their hydrolysis catalyzed by phosphodiesterases (PDEs). PDE regulation is quite potent—often suppressing an acute rise in a given cyclic nucleotide back to baseline within seconds. It is also compartmentalized within the cell, so that specific targeted proteins can be regulated by the same "generic" cyclic nucleotide. By virtue of its modulation of cGMP in the myocyte, PDE1 participates in hypertrophy regulation. (Circ Res. 2009, Nov. 6; 105(10):931).

One of the challenges currently faced in the field is the lack of PDE1 specific inhibitors. The current invention seeks to overcome this as well as other challenges in the art by providing PDE1 specific inhibitors. Although WO 2006/133261 and WO 2009/075784 provide PDE1 specific inhibitors, these do not disclose the compounds of the current invention.

SUMMARY OF THE INVENTION

PDE1 is up-regulated in chronic disease conditions such as atherosclerosis, cardiac pressure-load stress and heart failure, as well as in response to long-term exposure to nitrates. PDE1 inhibitors have relatively little impact on resting function, but rather maintain the ability to potently modulate acute contractile tone in cells stimulated by vasoactive agonists. Such up-regulation contributes to vascular and cardiac pathophysiology and to drug tolerance to nitrate therapies. Therefore, without being bound by theory, it is believed that compounds that modulate cGMP/PKG mediated pathways, such as PDE1 inhibitors, are particularly useful for reversing cardiac hypertrophy. The PDE1 inhibitors disclosed herein are selective PDE1 inhibitors having a limited ability to penetrate the blood brain barrier and therefore, are believed to have significant modulatory activity (e.g., enhancement of cGMP) in those areas of the body outside of the central nervous system where PDE1 isoforms are predominately located: e.g., cardiac, vascular, and lung tissue.

Therefore, in the first aspect, the invention provides a compound of Formula I:

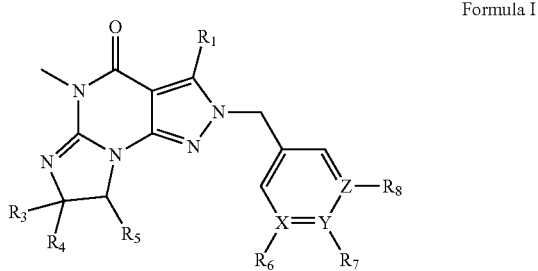

Formula I in free or salt form, wherein
(i) $R_1$ is $C_{1-4}$alkyl (e.g., methyl or ethyl), or —NH($R_2$), wherein $R_2$ is phenyl optionally substituted with halo (e.g., fluoro), for example, 4-fluorophenyl;
(ii) X, Y and Z are, independently, N or C;
(iii) $R_3$, $R_4$ and $R_5$ are independently H or $C_{1-4}$alkyl (e.g., methyl); or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively),
(iv) $R_6$, $R_7$ and $R_8$ are independently:
H,
$C_{1-4}$alkyl (e.g., methyl),
pyrid-2-yl substituted with hydroxy, or
—S(O)$_2$—NH$_2$;
(v) Provided that when X, Y and/or Z are N, then $R_6$, $R_7$ and/or $R_8$, respectively, are not present; and when X, Y and Z are all C, then at least one of $R_6$, $R_7$ or $R_8$ is —S(O)$_2$—NH$_2$ or pyrid-2-yl substituted with hydroxy.

In a particular embodiment, the invention provides a compound of Formula I as follows:
1.1 the compound of Formula I, wherein $R_1$ is $C_{1-4}$alkyl (e.g., methyl or ethyl) or —NH($R_2$) wherein $R_2$ is phenyl optionally substituted with halo (e.g., fluoro), for example, 4-fluorophenyl;
1.2 the compound of Formula I, wherein $R_1$ is $C_{1-4}$alkyl (e.g., methyl or ethyl);
1.3 the compound of Formula I, wherein $R_1$ is —NH($R_2$), wherein $R_2$ is phenyl optionally substituted with halo (e.g., fluoro);
1.4 the compound of Formula I, wherein $R_1$ is —NH($R_2$), wherein $R_2$ is phenyl;
1.5 the compound of Formula I, wherein $R_1$ is —NH($R_2$), wherein $R_2$ is phenyl substituted with halo (e.g., fluoro), for example, 4-fluorophenyl;
1.6 the compound of Formula I or any of formulae 1.1-1.5, wherein X, Y and Z are, independently, N or C;
1.7 the compound of Formula I or any of formulae 1.1-1.5, wherein X, Y and Z are all C;
1.8 the compound of Formula I or any of formulae 1.1-1.5, wherein at least one of X, Y and/or Z is N;
1.9 the compound of Formula I or any of formulae 1.1-1.5, wherein X is N;
1.10 the compound of Formula I or any of formulae 1.1-1.5, wherein Z is N;
1.11 the compound of Formula I or any of formulae 1.1-1.5, wherein Y is N;
1.12 the compound of Formula I or any of formulae 1.1-1.5, wherein X and Z are N and Y is C;
1.13 the compound of Formula I or any of formulae 1.1-1.12, wherein $R_6$, $R_7$ and $R_8$ are independently:
H,
$C_{1-4}$alkyl (e.g., methyl),
pyrid-2-yl substituted with hydroxy, or
—S(O)$_2$—NH$_2$;
1.14 the compound of Formula I or any of formulae 1.1-1.12, wherein one or more of $R_6$, $R_7$ and $R_8$ are independently H;
1.15 the compound of Formula I or any of formulae 1.1-1.12, wherein $R_6$, $R_7$ and $R_8$ are independently $C_{1-4}$alkyl (e.g., methyl);
1.16 formula 1.15, provided that when $R_6$, $R_7$ and/or $R_8$ are independently $C_{1-4}$alkyl (e.g., methyl), then X, Y, and/or Z, respectively, are C (or not N);
1.17 the compound of Formula I or any of formulae 1.1-1.12, wherein $R_6$, $R_7$ and $R_8$ are independently H or $C_{1-4}$alkyl (e.g., methyl);
1.18 the compound of Formula I or any of formulae 1.1-1.12, wherein $R_6$, $R_7$ and $R_8$ are independently pyrid-2-yl substituted with hydroxy;
1.19 the compound of Formula I or any of formulae 1.1-1.12, wherein $R_7$ is pyrid-2-yl substituted with hydroxy (e.g, 6-hydroxypyrid-2-yl);
1.20 formula 1.18 or 1.19, provided that when $R_6$, $R_7$ and/or $R_8$ are independently pyrid-2-yl substituted with hydroxy, then X, Y and/or Z, respectively are independently C (or not N);
1.21 the compound of Formula I or any of formulae 1.1-1.12, wherein one or more of $R_6$, $R_7$ and $R_8$ are independently —S(O)$_2$—NH$_2$;
1.22 the compound of Formula I or 1.7, wherein at least one of $R_6$, $R_7$ and $R_8$ is —S(O)$_2$—NH$_2$ or pyrid-2-yl substituted with hydroxy;
1.23 the compound of Formula I or 1.9, wherein $R_6$ does not exist and $R_7$ and $R_8$ are H;
1.24 the compound of Formula I or 1.10, wherein $R_8$ does not exist and $R_6$ and $R_7$ are H;
1.25 the compound of Formula I or 1.11, wherein $R_7$ does not exist and $R_6$ and $R_8$ are H;

1.26 the compound of Formula I or 1.12, wherein $R_6$ and $R_8$ do not exist and $R_7$ is $C_{1-4}$alkyl (e.g., methyl);

1.27 the compound of Formula I or 1.12, wherein $R_6$ and $R_8$ do not exist and $R_7$ is methyl;

1.28 the compound of Formula I or any of formula 1.1-1.27, wherein $R_3$, $R_4$ and $R_5$ are independently H or $C_{1-4}$alkyl; or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively);

1.29 the compound of Formula I or any of formula 1.1-1.27, wherein $R_3$, $R_4$ and $R_5$ are independently H or $C_{1-4}$alkyl;

1.30 the compound of Formula I or any of formula 1.1-1.27, wherein $R_3$ and $R_4$ are independently $C_{1-4}$alkyl and $R_5$ is H;

1.31 the compound of Formula I or any of formula 1.1-1.27, wherein $R_3$ and $R_4$ are both methyl and $R_5$ is H;

1.32 the compound of Formula I or any of formula 1.1-1.27, wherein $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively);

1.33 the compound of formula 1.32, wherein the $R_4$ and $R_5$ together have the cis configuration, e.g., where the carbons carrying $R_4$ and $R_5$ have the R and S configurations, respectively);

1.34 the compound of Formula I, wherein:
  (i) $R_1$ is —N($R_2$), wherein $R_2$ is phenyl optionally substituted with halo (e.g., fluoro), for example, 4-fluorophenyl;
  (ii) At least one of X, Y and Z is N;
  (iii) $R_3$, $R_4$ and $R_5$ are independently H or $C_{1-4}$alkyl; or $R_3$ is H and $R_4$ and $R_5$ together form a tri-methylene bridge (pref. wherein the $R_4$ and $R_5$ together have the cis configuration, e.g., where the carbons carrying $R_4$ and $R_5$ have the R and S configurations, respectively),
  (iv) $R_6$, $R_7$ and $R_8$ are independently H or $C_{1-4}$alkyl (e.g., methyl);

1.35 the compound of Formula I or 1.34, wherein $R_3$, $R_4$ and $R_5$ are independently H or $C_{1-4}$alkyl (e.g., methyl);

1.36 the compound of Formula I or 1.34 or 1.35, wherein $R_3$ and $R_4$ are independently $C_{1-4}$alkyl (e.g., $R_3$ and $R_4$ are methyl), and $R_5$ is H;

1.37 the compound of Formula I, wherein:
  $R_1$ is —N($R_2$), wherein $R_2$ is phenyl optionally substituted with halo (e.g., fluoro), for example, 4-fluorophenyl;
  X and Z are N and Y is C;
  $R_7$ is $C_{1-4}$alkyl (e.g., methyl);
  $R_3$ and $R_4$ are $C_{1-4}$alkyl (e.g., methyl);
  $R_5$ is H;

1.38 the compound according to any of the above formulae, selected from the group consisting of:

3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one;

3-((4-fluorophenyl)amino)-5,7,7-trimethyl-2-(pyridin-3-ylmethyl)-7,8-dihydro-2H-imidazo[1,2-a]pyrazolo[4,3-e]pyrimidin-4(5H)-one;

3-((4-fluorophenyl)amino)-5,7,7-trimethyl-2-(pyridin-4-ylmethyl)-7,8-dihydro-2H-imidazo[1,2-a]pyrazolo[4,3-e]pyrimidin-4(5H)-one;

(6aR,9aS)-2-(4-(6-hydroxypyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4(2H)-one;

4-(((6aR,9aS)-5-methyl-4-oxo-3-(phenylamino)-4,5,7,8,9,9a-hexahydrocyclopenta[4,5]imidazo[1,2-a]pyrazolo[4,3-e]pyrimidin-2(6aH)-yl)methyl)benzenesulfonamide;

3-((4-fluorophenyl)amino)-5,7,7-trimethyl-2-((6-methylpyridin-3-yl)methyl)-7,8-dihydro-2H-imidazo[1,2-a]pyrazolo[4,3-e]pyrimidin-4(5H)-one;

4-((3-((4-fluorophenyl)amino)-5,7,7-trimethyl-4-oxo-4,5,7,8-tetrahydro-2H-imidazo[1,2-a]pyrazolo[4,3-e]pyrimidin-2-yl)methyl)benzenesulfonamide;

3-((4-fluorophenyl)amino)-2-(4-(6-hydroxypyridin-2-yl)benzyl)-5,7,7-trimethyl-7,8-dihydro-2H-imidazo[1,2-a]pyrazolo[4,3-e]pyrimidin-4(5H)-one;

2-(4-(6-hydroxypyridin-2-yl)benzyl)-3,5,7,7-tetramethyl-7,8-dihydro-2H-imidazo[1,2-a]pyrazolo[4,3-e]pyrimidin-4(5H)-one;

3-ethyl-2-(4-(6-hydroxypyridin-2-yl)benzyl)-5,7,7-trimethyl-7,8-dihydro-2H-imidazo[1,2-a]pyrazolo[4,3-e]pyrimidin-4(5H)-one;

1.39 any of the preceding formulae wherein the compounds inhibit phosphodiesterase-mediated (e.g., PDE1-mediated) hydrolysis of cGMP, e.g., with an $IC_{50}$ of less than 1 μM, preferably less than 75 nM, preferably less than 1 nM, in an immobilized-metal affinity particle reagent PDE assay, for example, as described in Example 11;

in free or salt form, provided that when X, Y and/or Z are N, then $R_6$, $R_7$ and/or $R_8$, respectively, are not present; and when X, Y and Z are all C, then at least one of $R_6$, $R_7$ or $R_8$ is —S(O)$_2$—NH$_2$ or pyrid-2-yl substituted with hydroxy.

In the second aspect, the invention provides a pharmaceutical composition comprising the compound of Formula I or any of 1.1-1.39 as described herein, in free or pharmaceutically acceptable salt form, in admixture (or in combination or association) with a pharmaceutically acceptable diluents or carrier.

The compound of Formula I or any of 1.1-1.39 as described herein are selective PDE1 inhibitors and therefore are useful for regulating cGMP/PKG in cardiac hypertrophy. Previous studies have demonstrated that increases in intracellular $Ca^{2+}$/CaM-dependent signaling promote maladaptive hypertrophic gene expression in cardiomyocytes through various effectors such as the protein phosphatase calcineurin, $Ca^{2+}$/CaM-dependent kinase II (CaMKII). Without being bound by any theory, increases in endogenous cGMP/PKG-dependent signaling may be able to decrease cardiac hypertrophy, by suppressing Gq/11 activation and normalizing $Ca^{2+}$ signaling. By activating PDE1, $Ca^{2+}$/CaM may decrease cGMP levels and PKG activity. In turn, this process may drive cardiac hypertrophy. Additionally, up-regulation of PDE1 expression upon neurohumoral or biomechanical stress during cardiac hypertrophy may further enhance PDE1 activity and attenuate cGMP/PKG signaling. Accordingly, without being bound by any theory, it is believed that inhibition of PDE1A could, for example, reverse or prevent the attenuation of cGMP/PKG signaling. As discussed previously, PDE1B is also implicated in the inflammatory component of heart disease (e.g., PDE1B2 is up-regulated during the process of differentiation of macrophages, as occurs during heart disease progression). Similarly, PDE1C is induced in human arterial smooth muscle cells of the synthetic, proliferative phenotype. Therefore, administration of a PDE1 inhibitor as described herein could provide a potential means to regulate cardiac hypertrophy, and by extension provide a treatment for various cardiovascular diseases and disorders.

Therefore, in the third aspect, the invention provides a method for the treatment or prophylaxis of a disease or disorder which may be ameliorated by modulating (e.g., enhancing) cGMP/PKG-dependent signaling pathways (e.g., in cardiac tissue), e.g. a cardiovascular disease or disorder, comprising administering to a patient in need thereof an effective amount of the compound of Formula I or any of formulae 1.1-1.39 as described herein, in free or pharmaceutically acceptable salt form.

The cardiovascular disease or disorder may be selected from a group consisting of: hypertrophy (e.g., cardiac hypertrophy), atherosclerosis, myocardial infarction, congestive heart failure, angina, stroke, hypertension, essential hypertension, pulmonary hypertension, pulmonary arterial hypertension, secondary pulmonary hypertension, isolated systolic hypertension, hypertension associated with diabetes, hypertension associated with atherosclerosis, renovascular hypertension. In certain embodiments, the cardiovascular disease or disorder to be treated may also relate to impaired cGMP/PKG-dependent signaling. In a particular embodiment, the invention provides a method for the treatment or prevention of stroke, wherein the PDE1 inhibitor, through its effect on the endothelial cells of cerebral capillaries, is able to promote increased cerebral blood flow.

In a further embodiment of the third aspect, the invention also provides a method for the treatment or prophylaxis of cardiovascular disease or disorder that is associated with a muscular dystrophy (e.g, Duchenne, Becker, limb-girdle, myotonic, and Emery-Dreifuss Muscular Dystrophy) comprising administering to a patient in need thereof an effective amount of the compound of Formula I or any of 1.1-1.39 as described herein, in free or pharmaceutically acceptable salt form. As noted above, DMD is caused by the absence of a functional dystrophin protein, which in turn leads to reduced expression and mis-localization of dystrophin-associated proteins, such as neuronal nitric oxide (NO) synthase. Disruption of nNOS signaling may result in muscle fatigue and unopposed sympathetic vasoconstriction during exercise, thereby increasing contraction-induced damage in dystrophin-deficient muscles. Without being bound by theory, the loss of normal nNOS signaling during exercise may be central to the vascular dysfunction proposed to be an important pathogenic mechanism in DMD. It is contemplated that by inhibiting phosphodiesterases (e.g. PDE1), the compounds described herein may circumvent defective nNOS signaling in dystrophic skeletal and/or cardiac muscle; thereby potentially improving cardiac outcomes in DMD patients.

In still another embodiment, the invention provides for the treatment of renal failure, fibrosis, inflammatory disease or disorders, vascular remodeling and connective tissue diseases or disorders (e.g., Marfan Syndrome), comprising administering to a patient in need thereof an effective amount of the compound of Formula I or any of formulae 1.1-1.39 as described herein, in free or pharmaceutically acceptable salt form.

The PDE1 compounds of the invention useful for the treatment or prophylaxis of disease according to the foregoing methods may be used as a sole therapeutic agent or may be used in combination with one or more other therapeutic agents useful for the treatment of cardiovascular disorders. Such other agents include angiotensin II receptor antagonists, angiotensin-converting-enzyme (ACE) inhibitors, neutral endopeptidase (NEP or Neprilysin) inhibitors and/or phosphodiesterase 5 (PDE5) inhibitors.

Therefore, in a particular embodiment, the PDE1 inhibitor of the invention may be administered in combination with an angiotensin II receptor antagonist selected from azilsartan, candesartan, eprosartan, irbesartan, losartan, olmesartan, olmesartan medoxomil, saralasin, telmisartan and valsartan, in free or pharmaceutically acceptable salt form.

In yet another embodiment, the PDE1 inhibitor of the invention may be administered in combination with an angiotensin-converting-enzyme (ACE) inhibitor selected from the group consisting of: captopril, enalapril, lisinopril, benazepril, ramipril, quinapril, perindopril, imidapril, trandolapril and cilazapril, in free or pharmaceutically acceptable salt form.

In still another particular embodiment, the PDE1 inhibitor of the invention may be administered in combination with a PDE5 inhibitor selected from avanafil, lodenafil, mirodenafil, tadalafil, vardenafil, udenafil and zaprinast, in free or pharmaceutically acceptable salt form.

In still another particular embodiment, the PDE1 inhibitor of the invention may be administered in combination with a neutral endopeptidase (NEP or Neprilysin) inhibitor. Neutral endopeptidase, also known as Neprilysin or NEP (EC 3.4.24.11), is a type II integral membrane zinc-dependent metalloendoprotease that cleaves a variety of short peptide substrates. In mammals, NEP is widely expressed, including in the kidney, lung, endothelial cells, vascular smooth muscle cells, cardiac myocytes, fibroblasts, adipocytes and brain. Among its natural targets are cardiac atrial natriuretic peptide (ANP), B-type natriuretic peptide (BNP), C-type natriuretic peptide (CNP), angiotensin I (Ang-I), angiotensin II (Ang-II), bradykinin (BK), and endothelin (ET). Cleavage of these peptides by NEP results in their inactivation, attenuating the peptides' natural biological effects.

ANP, BNP and CNP are all part of the natriuretic peptide (NP) system, which, along with the renin-angiotensin system, is a major components of mammalian blood pressure homeostasis. While the renin-angiotensin system is primarily responsible for increasing blood pressure (e.g., by promoting vasoconstriction and water retention), the natriuretic peptide system is primarily responsible for decreasing blood pressure (e.g., by promoting vasodilation and natriuresis). ANP and BNP are both powerful vasodilators and strong promoters of decreased renal reabsorption of sodium and water in a potassium-sparing manner. These dual effects exert a powerful blood pressure lowering effect. BNP and CNP also exert an anti-fibrotic effect and an anti-hypertrophic effect in the heart. CNP shares the vasodilatory effects of ANP/BNP but without the renal effects.

In addition, both hypertension and obesity have been shown to be associated with reduced ANP and BNP levels, and a specific genetic variant of ANP (rs5068), which increases ANP levels, has been shown to protect against hypertension and metabolic syndrome. Thus, ANP, BNP and CNP play an important role in blood pressure homeostasis and cardiovascular health.

Inhibition of NEP results in an increase in the half-lives of circulating ANP, BNP and CNP. This is expected to prolong their blood-pressure lowering and cardiac health improving effects. Urine cAMP levels are significantly elevated after systemic administration of NEP inhibitors.

Inhibition of NEP also results in higher levels of bradykinin, angiotensin I, angiotensin II and endothelin. Importantly, endothelin and angiotensin II are strongly pro-hypertensive peptides. Thus, NEP inhibition alone results in both vasodilatory effects (from the NPs) and vasoconstrictive effects (from increased Ang-II and ET). These pro-hypertensive peptides all operate via binding to G-protein coupled receptors (GPCRs). The major contributor to this vasoconstrictive effect is Angiotensin-II, which operates via binding to the G-protein coupled receptors $AT_1$ and $AT_2$. These receptors exert their physiological effects through activation of phospholipase C (PLC) and protein kinase C (PKC) signaling cascades. Bradykinin is inactivated to a large extent by ACE, and ACE inhibitors cause congestion as a major side effect, which is not seen with NEP inhibitors.

ANP, BNP and CNP all function via the second messenger cGMP. ANP and BNP bind to membrane-bound guanylyl cyclase-A, while CNP binds to guanylyl cyclase B. Both of these enzymes increase intracellular cGMP in response to receptor binding. The increased cGMP concentration activates protein kinase G (PKG) which is responsible for exerting the downstream biological effects of the natriuretic peptides.

Several NEP inhibitors are known, including candoxatril, candoxatrilat, omapatrilat, gempatrilat, and sampatrilat. Candoxatril had been shown to produce a dose-dependent increase in both plasma ANP and cGMP levels, and although it is safe, it does not produce a stable blood-pressure lowering effect. This is thought to be due to the effects of NEP inhibition on BK, ET and Ang-II breakdown. Candoxatril treatment in patients with heart failure has been shown to increase levels of endothelin significantly, thus cancelling out the blood pressure effects caused by increased ANP.

In contrast to candoxatril and candoxatrilat, omapatrilat is considered a vasopeptidase inhibitor (VPI), because it functions to an equal extent as both an NEP inhibitor and an ACE (angiotensin converting enzyme) inhibitor. ACE is the enzyme that is responsible for converting Ang-I to Ang-II, which is the major pro-hypertensive hormone of the renin-angiotensin system. By inhibiting both NEP and ACE, it was thought that the increase in Ang-II caused by NEP inhibition would be negated, resulting in a highly effective antihypertensive treatment. Clinical studies, however, showed that omapatrilat was associated with a severe incidence of angioedema (a known side effect of ACE inhibitors). Later research has indicated that this may be due to concomitant inhibition of aminopeptidase P (APP). ACE, APP and NEP all contribute to the breakdown of bradykinin, which is another anti-hypertensive peptide, and the over-accumulation of bradykinin resulting from simultaneous inhibition of three of its degradation pathways may be a strong factor leading to angioedema.

Without intending to be bound by any particular theory, the combination of a PDE1 inhibitor with a selective NEP inhibitor (not a VPI) should realize the full positive effects of NEP inhibition (increased ANP, BNP and CNP half-life), further enhanced by the potentiation of the NP signaling cascades (mediated by cGMP) caused by PDE1 inhibition, without the negative effects of NEP inhibition that can lead to decreased efficacy.

Therefore, in a particular embodiment, the neutral endopeptidase (NEP or Neprilysin) inhibitor useful for the invention is a selective NEP inhibitor, e.g., with at least 300-fold selectivity for NEP inhibition over ACE inhibition. In a further embodiment, the NEP inhibitors for use in the current invention are inhibitors with at least 100-fold selectivity for NEP inhibition over ECE (Endothelin Converting Enzyme) inhibition. In yet another embodiment, the NEP inhibitors for use in the current invention are inhibitors with at least 300-fold selectivity for NEP inhibition over ACE inhibition and 100-fold selectivity for NEP inhibition over ECE inhibition.

In another embodiment, the NEP inhibitors for use in the current invention are the NEP inhibitors disclosed in the following publications: EP-1097719 B1, EP-509442A, U.S. Pat. No. 4,929,641, EP-599444B, U.S. Pat. No. 798,684, *J. Med. Chem.* (1993) 3821, EP-136883, U.S. Pat. No. 4,722,810, *Curr. Pharm. Design* (1996) 443, *J. Med. Chem.* (1993) 87, EP-830863, EP-733642, WO 9614293, WO 9415908, WO 9309101, WO 9109840, EP-519738, EP-690070, *Bioorg. Med. Chem. Lett.* (1996) 65, EP-A-0274234, *Biochem. Biophys. Res. Comm.* (1989) 58, *Perspect. Med. Chem.* (1993) 45, or EP-358398-B. The contents of these patents and publications are hereby incorporated by reference in their entirety herein.

In still another embodiment, the NEP inhibitors useful in the current invention are the NEP inhibitors Phosphoramidon, Thiorphan, Candoxatrilat, Candoxatril, or the compound of the Chemical Abstract Service (CAS) Number 115406-23-0.

In yet another embodiment, the NEP inhibitors useful in the current invention are the NEP inhibitors disclosed in US 2006/0041014 A1, the contents of which are hereby incorporated by reference in their entirety herein.

In another embodiment, the NEP inhibitors useful in the current invention are the NEP inhibitors disclosed in U.S. Pat. No. 5,217,996, the contents of which are hereby incorporated by reference in their entirety herein.

In another embodiment, the NEP inhibitors useful in the current invention are the NEP inhibitors disclosed in U.S. Pat. No. 8,513,244, the contents of which are hereby incorporated by reference in their entirety herein.

In another embodiment, the NEP inhibitors useful in the current invention are the NEP inhibitors disclosed in U.S. Pat. No. 5,217,996, the contents of which are hereby incorporated by reference in their entirety herein.

In another embodiment, the NEP inhibitors useful in the current invention are the NEP inhibitors disclosed in US patent application publication 2013/0330365, the contents of which are hereby incorporated by reference in their entirety herein.

In another embodiment, the NEP inhibitor useful in the current invention is 3-[{1S, 3R}-1-biphenyl-4ylmethyl-3-ethoxycarbonyl-1-butylcarbamoyl]propionic acid,

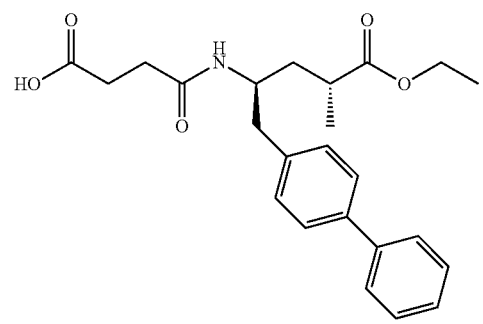 [SMILES: CCOC(=O)[C@H](C)C[C@@H](Cc1ccc(-c2ccccc2)cc1)NC(=O)CCC(=O)O]

also known as AHU-377, in free or a pharmaceutically acceptable salt or prodrug, thereof, and in a preferred embodiment thereof, in sodium salt form.

In another embodiment, the NEP inhibitor useful in the current invention is [{1S, 3R}-1-biphenyl-4ylmethyl-3-carboxy-1-butylcarbamoyl]propionic acid,

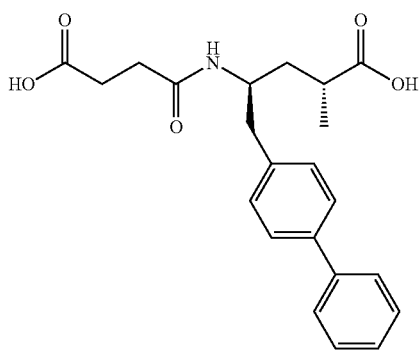 [SMILES: C[C@H](C[C@@H](Cc1ccc(-c2ccccc2)cc1)NC(=O)CCC(=O)O)C(=O)O]

also known as LBQ-657, in free or pharmaceutically acceptable ester, salt or prodrug form.

In another embodiment, the NEP inhibitor useful in the current invention is selected from among the following: sampatrilat, fasidotril, Z13752A, MDL 100240, BMS 189921, LBQ657, AHU-377, or mixanpril, in free or pharmaceutically acceptable salt form or in prodrug form thereof.

In another embodiment, the NEP inhibitor for use in the current invention is selected from the following:
SQ 28,603;
N—[N-[1(S)-carboxy-3-phenylpropyl]-(S)-phenylalanyl]-(S)-isoserine;
N—[N-[((1S)-carboxy-2-phenyl)ethyl]-(S)-phenylalanyl]-beta-alanine;
N-[(2S)-mercaptomethyl-3-(2-methylphenyl)-propionyl] methionine;
(cis-4-[[[1-[2-carboxy-3-(2-methoxy-ethoxy)propyl]-cyclopentyl]carbonyl]amino]-cyclohexanecarboxylic acid);
thiorphan; retro-thiorphan; phosphoramidon; SQ 29072;
N-(3-carboxy-1-oxopropyl)-(4S)-p-phenylphenylmethyl)-4-amino-2R-methylbutanoic acid ethyl ester;
(S)-cis-4-[1-[2-(5-indanyloxycarbonyl)-3-(2-methoxyethoxy)propyl]-1-cyclopentanecarboxamido]-1-cyclohexanecarboxylic acid;
3-(1-[6-endo-hydroxymethyl-bicyclo[2,2,1]heptane-2-exo-carbamoyl]cyclopentyl)-2-(2-methoxyethyl)propanoic acid;
N-(1-(3-(N-t-butoxycarbonyl-(S)-prolylamino)-2(S)-t-butoxy-carbonylpropyl) cyclopentanecarbonyl)-O-benzyl-(S)-serine methyl ester;
4-[[2-(mercaptomethyl)-1-oxo-3-phenylpropyl]amino]benzoic acid;
3-[1-(cis-4-carboxycarbonyl-cis-3-butylcyclohexyl-r-1-carbamoyl)cyclopentyl]-2S-(2-methoxyethoxymethyl)propanoic acid;
N-((2S)-2-(4-biphenylmethyl)-4-carboxy-5-phenoxyvaleryl)glycine;
N-(1-(N-hydroxycarbamoylmethyl)-1-cyclopentanecarbonyl)-L-phenylalanine;
(S)-(2-biphenyl-4-yl)-1-(1H-tetrazol-5-yl)ethylamino)methylphosphonic acid;
(S)-5-(N-(2-(phosphonomethylamino)-3-(4-biphenyl)propionyl)-2-aminoethyl)tetrazole;
beta-alanine;
3-[1,1'-biphenyl]-4-yl-N-[diphenoxyphosphinyl)methyl]-L-alanyl;
N-(2-carboxy-4-thienyl)-3-mercapto-2-benzylpropanamide;
2-(2-mercaptomethyl-3-phenylpropionamido)thiazol-4-yl-carboxylic acid;
(L)-(1-((2,2-dimethyl-1,3-dioxolan-4-yl)-methoxy)carbonyl)-2-phenethyl)-L-phenylalanyl)-beta-alanine;
N—[N-[(L)-[1-[(2,2-dimethyl-1,3-dioxolan-4-yl)-methoxy]carbonyl]-2-phenylethyl]-L-phenylalanyl]-(R)-alanine;
N—[N-[(L)-1-carboxy-2-phenylethyl]-L-phenylalanyl]-(R)-alanine;
N-[2-acetylthiomethyl-3-(2-methyl-phenyl)propionyl]-methionine ethyl ester;
N-[2-mercaptomethyl-3-(2-methylphenyl)propionyl]-methionine;
N-[(2S)-mercaptomethyl-3-(2-methylphenyl)propanoyl]-(S)-isoserine;
N—(S)-[3-mercapto-2-(2-methylphenyl)propionyl]-(S)-2-methoxy-(R)-alanine;
N-[1-[[(1S)-benzyloxy-carbonyl-3-phenylpropyl]amino]cyclopentylcarbonyl]-(S)-isoserine;
N-[1-[[(1S)-carbonyl-3-phenylpropyl]amino]-cyclopentyl-carbonyl]-(S)-isoserine;
1, 1'-[dithiobis-[(2S)-(2-methylbenzyl)-1-oxo-3,1-propanediyl]]-bis-(S)-isoserine;
1, 1'-[dithiobis-[(2S)-(2-methylbenzyl)-1-oxo-3, 1-propanediyl]]-bis-(S)-methionine;
N-(3-phenyl-2-(mercaptomethyl)-propionyl)-(S)-4-(methylmercapto)methionine;
N-[2-acetylthiomethyl-3-phenyl-propionyl]-3-aminobenzoic acid;
N-[2-mercaptomethyl-3-phenyl-propionyl]-3-aminobenzoic acid;
N-[1-(2-carboxy-4-phenylbutyl)-cyclopentane-carbonyl]-(S)-isoserine;
N-[1-(acetylthiomethyl)cyclopentane-carbonyl]-(S)-methionine ethyl ester;
(3S)-[2-(acetylthiomethyl)-3-phenyl-propionyl]amino-epsilon-caprolactam;
N-(2-acetylthiomethyl-3-(2-methylphenyl)propionyl)-methionine ethyl ester;
in free or pharmaceutically acceptable salt form.

In another aspect, the invention provides the following:
(i) the compound of Formula I or any of 1.1-1.39 as described herein, in free or pharmaceutically acceptable salt form, for use in any of the methods or in the treatment or prophylaxis of any disease or disorder as set forth herein,
(ii) a combination as described hereinbefore, comprising a PDE1 inhibitor of the invention, e.g., the compound of Formula I or any of 1.1-1.39 as described herein, in free or pharmaceutically acceptable salt form and a second therapeutic agent useful for the treatment of cardiovascular disorders, e.g., selected from angiotensin II receptor antagonist, angiotensin-converting-enzyme (ACE) inhibitor, neutral endopeptidase (NEP or Neprilysin) inhibitor and/or phosphodiesterase 5 (PDE5) inhibitor, in free or pharmaceutically acceptable salt form;
(iii) use of the compound of Formula I or any of 1.1-1.39, in free or pharmaceutically acceptable salt form, or the combination described herein, (in the manufacture of a medicament) for the treatment or prophylaxis of any disease or condition as set forth herein,
(iv) the compound of Formula I or any of 1.1-1.39, in free or pharmaceutically acceptable salt form, the combination described herein or the pharmaceutical composition of the invention as hereinbefore described for use in the treatment or prophylaxis of any disease or condition as set forth herein.

DETAILED DESCRIPTION OF THE INVENTION

If not otherwise specified or clear from context, the following terms herein have the following meanings:

(a) "Alkyl" as used herein is a saturated or unsaturated hydrocarbon moiety, preferably saturated, preferably having one to six carbon atoms, in some embodiment, one to four carbon atoms, which may be linear or branched, and may be optionally mono-, di- or tri-substituted, e.g., with halogen (e.g., chloro or fluoro) or hydroxy.

The term "optionally substituted with" is intended to be either substituted with a substituent or unsubstituted. In one embodiment, the invention is substituted. In another embodiment, the invention is unsubstituted.

Compounds of the Invention, e.g., the compound of Formula I or any of formulae 1.1-1.39 as described herein, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

The Compounds of the Invention include their enantiomers, diastereomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Methods of Using Compounds of the Invention

The Compounds of the Invention are useful in the treatment of diseases characterized by disruption of or damage to cGMP/PKG mediated pathways, e.g., as a result of increased expression of PDE1 or decreased expression of cGMP/PKG activity due to inhibition or reduced levels of inducers of cyclic nucleotide synthesis, such as dopamine and nitric oxide (NO). It is believed that by inhibiting PDE1A or PDE1C, for example, that this action could reverse or prevent the attenuation of cGMP/PKG signaling (e.g., enhance cGMP) and that this action could modulate cardiac hypertrophy. Therefore, administration or use of the PDE1 inhibitor as described herein, e.g., a Compound of Formula 1.1-1.39 as described herein, in free or pharmaceutically acceptable salt form, could provide a potential means to regulate cardiac hypertrophy (e.g., prevent and/or reverse cardiac hypertrophy), and in certain embodiments provide a treatment for various cardiovascular diseases and disorders.

The PDE1 inhibitors of the present invention generally are selective for PDE1 (generally off-target interactions >10×, more preferably >25×, still more preferably >100× affinity for PDE1), exhibit good oral availability in plasma with very minimal brain penetration in mice. The blood/plasma ratio in mice administered the PDE1 inhibitors of the present invention is preferably less than 0.4, more preferably less than 0.2, more preferably less than or equal to 0.1.

The PDE1 inhibitor of the invention (i.e., Formula I as hereinbefore described) may be used in a combination therapy wherein the PDE1 inhibitor may be administered simultaneously, separately or sequentially with another active agent. Therefore, the combination can be a free combination or a fixed combination.

The term "simultaneously" when referring to a therapeutic use means administration of two or more active ingredients at or about the same time by the same route of administration.

The term "separately" when referring to a therapeutic use means administration of two or more active ingredients at or about the same time by different route of administration.

The dosages of a compound of the invention in combination with another active agent can be the same as or lower than the approved dosage for the drug, the clinical or literature test dosage or the dosage used for the drug as a monotherapy. The dosage amount will be apparent to one skilled in the art.

Diseases and disorders that may be prevented or ameliorated by the enhancement of cGMP/PKG signaling (e.g., cardiovascular disease), e.g., using the Compound of the Invention as described herein, include, but are not limited to: hypertrophy (e.g., cardiac hypertrophy), atherosclerosis, myocardial infarction, congestive heart failure, angina, stroke, hypertension, essential hypertension, pulmonary hypertension, pulmonary arterial hypertension, secondary pulmonary hypertension, isolated systolic hypertension, hypertension associated with diabetes, hypertension associated with atherosclerosis, renovascular hypertension, renal failure, fibrosis, an inflammatory disease or disorder, vascular remodeling, and an connective tissue disease or disorder (e.g., Marfan Syndrome).

In one embodiment, the Compounds of the Invention as described herein are useful in the treatment or prevention of stroke by treating or preventing transient ischemic attacks (TIA). Without being bound by any theory, it is believed that the Compounds of the Invention may prevent or treat the risk of transient ischemic attacks by actually increasing the amount and/or concentration of blood flow to the brain. It is contemplated that the compounds as described herein could increase the blood flow to the brain without significant passage across the blood brain barrier.

In another embodiment, the invention further provides using the Compounds of the Invention for the treatment or prevention of disease or disorder as follows: Duchenne muscular dystrophy, Becker muscular dystrophy, limb-girdle muscular dystrophy, myotonic dystrophy, and Emery-Dreifuss muscular dystrophy. In one embodiment, the Compounds of the Invention are useful in treating cardiac dysfunction associated with aforementioned types of muscular dystrophy. In another embodiment, the Compounds of the Invention may potentially reduce or reverse the cardiac hypertrophy that may be associated with these aforementioned types of muscular dystrophy.

"PDE1 inhibitor" as used herein describes a compound of Formula I or any of formulae 1.1-1.39 which selectively inhibit phosphodiesterase-mediated (e.g., PDE1-mediated, especially PDE1B-mediated) hydrolysis of cGMP, e.g., with an $IC_{50}$ of less than 1 µM, preferably less than 75 nM, preferably less than 1 nM, in an immobilized-metal affinity particle reagent PDE assay as described or similarly described in Example 1.

The phrase "Compounds of the Invention" or "PDE1 inhibitors of the Invention", or like terms, encompasses any and all of the compounds disclosed herewith, e.g., a Compound of Formula I or any of formulae 1.1-1.39, in free or salt form.

The words "treatment" and "treating" are to be understood accordingly as embracing treatment or amelioration of symptoms of disease as well as treatment of the cause of the disease.

For methods of treatment, the word "effective amount" is intended to encompass a therapeutically effective amount to treat a specific disease or disorder.

The term "patient" include human or non-human (i.e., animal) patient. In particular embodiment, the invention encompasses both human and nonhuman. In another embodiment, the invention encompasses nonhuman. In other embodiment, the term encompasses human.

The term "comprising" as used in this disclosure is intended to be open-ended and does not exclude additional, unrecited elements or method steps.

Compounds of the Invention, e.g., compounds of Formula I or any of formulae 1.1-1.39 as hereinbefore described, in free or pharmaceutically acceptable salt form, may be used as a sole therapeutic agent, but may also be used in combination or for co-administration with other active agents.

Dosages employed in practicing the present invention will of course vary depending, e.g. on the particular disease or condition to be treated, the particular compound used, the mode of administration, and the therapy desired. The compound may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 300 mg, conveniently administered once, or in divided doses 2 to 4 times, daily or in sustained release form. Unit dosage forms for oral administration thus for example may comprise from about 0.2 to 75 or 150 mg or 300 mg, e.g. from about 0.2 or 2.0 to 10, 25, 50, 75, 100, 150, 200 or 300 mg of the compound disclosed herein, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

Methods of Making Compounds of the Invention

The compounds of the Invention and their pharmaceutically acceptable salts may be made using the methods as described and exemplified herein and/or by methods similar thereto and/or by methods known in the chemical art. Such methods include, but not limited to, those described below. If not commercially available, starting materials for these processes may be made by procedures, which are selected from the chemical art using techniques which are similar or analogous to the synthesis of known compounds.

Various NEP inhibitors and starting materials therefor may be prepared using methods described in US 2006-0041014 A1, EP 1097719 A1, U.S. Pat. No. 8,513,244, and US 2013-0330365 A1. All references cited herein are hereby incorporated by reference in their entirety.

Various starting materials and/or Compounds of the Invention may be prepared using methods described in WO 2006/133261 and WO 2009/075784. All references cited herein are hereby incorporated by reference in their entirety.

Terms and Abbreviations

DMF=N,N-dimethylforamide,
MeOH=methanol,

THF=tetrahydrofuran,
equiv.=equivalent(s),
h=hour(s),
HPLC=high performance liquid chromatography,
LiHMDS=lithium bis(trimethylsilyl)amide,
NMP=1-methyl-2-pyrrolidinone,
Pd$_2$(dba)$_3$=tris[dibenzylideneacetone]dipalladium(0),
TFA=trifluoroacetic acid,
TFMSA=trifluoromethanesulfonic acid
XantPhos=4,5-bis(diphenylphosphino)-9,9-dimethylxanthene

EXAMPLES

Example 1: 3-((4-fluorophenyl)amino)-5,7,7-trimethyl-2-(pyridin-4-ylmethyl)-7,8-dihydro-2H-imidazo[1,2-a]pyrazolo[4,3-e]pyrimidin-4(5H)-one

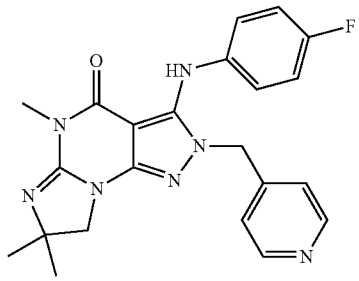 [SMILES: CN1C(=O)c2c(nn(Cc3ccncc3)c2Nc2ccc(F)cc2)N2CC(C)(C)N=C12]

(a) 2-(4-Bromobenzyl)-7-(4-methoxybenzyl)-5-methyl-2H-pyrazolo[3,4-d]pyrimidine-4,6(5H,7H)-dione A suspension of 7-(4-methoxybenzyl)-5-methyl-2H-pyrazolo[3,4-d]pyrimidine-4,6(5H,7H)-dione (161 g, 562 mmol), 1-bromo-4-(bromomethyl) benzene (157 g, 628 mmol) and K$_2$CO$_3$ (93.2 g, 674 mmol) in DMF (800 mL) is stirred at room temperature until the reaction is complete. The reaction mixture is poured into water (5 L). After filtration, the filter cake is washed with water and ethanol successively, and then dried under vacuum to give 226 g of product (yield: 88%). MS (ESI) m/z 455.1 [M+H]$^+$.

(b) 2-(4-Bromobenzyl)-5-methyl-2H-pyrazolo[3,4-d]pyrimidine-4,6(5H,7H)-dione

TFA (500 mL) is slowly added into a suspension of 2-(4-bromobenzyl)-7-(4-methoxybenzyl)-5-methyl-2H-pyrazolo[3,4-d]pyrimidine-4,6(5H,7H)-dione (226 g, 496 mmol) in methylene chloride (320 mL), and then TFMSA (160 mL) is added slowly. The reaction mixture is stirred at room temperature overnight. Solvents are removed under reduced pressure. The obtained residue is treated with water (4 L) and ethyl acetate (2 L), stirred at room temperature for 30 min, and then filtered. The filter cake is thoroughly washed with water to remove residual acids, followed by washing with ethyl acetate. The obtained white solids are dried in a heated oven to give 159 g of product (yield: 96%). MS (ESI) m/z 335.0 [M+H]$^+$.

(c) 6-Chloro-5-methyl-2-(4-bromobenzyl)-2H-pyrazolo[3,4-d]pyrimidin-4(5H)-one 2-(4-Bromobenzyl)-5-methyl-2H-pyrazolo[3,4-d]pyrimidine-4,6(5H,7H)-dione (159 g, 475 mmol) is suspended in POCl$_3$ (300 mL), and then slowly heated to reflux. After the mixture is refluxed for 60 h, POCl$_3$ is removed under reduced pressure. The obtained residue is dissolved in methylene chloride (5 L), cooled to 0° C., and then adjusted to pH 8-9 with saturated sodium bicarbonate. After filtration, the obtained solids are washed with water twice, and then dried under vacuum to give 157 g of product (yield: 94%). MS (ESI) m/z 353.0 [M+H]$^+$.

(d) 6-(1-Hydroxy-2-methylpropan-2-ylamino)-5-methyl-2-(4-bromobenzyl)-2H-pyrazolo[3,4-d]pyrimidin-4(5H)-one A mixture of 6-chloro-5-methyl-2-(4-bromobenzyl)-2H-pyrazolo[3,4-d]pyrimidin-4(5H)-one (157 g, 444 mmol) and 2-amino-2-methylpropan-1-ol (236 g, 2.65 mol) in NMP (1.3 L) is heated at 120-125° C. for 2 h, and then poured into cold water. After filtration, the filter cake is washed with water twice, and then dried under vacuum to give 134 g of product (yield: 74%). MS (ESI) m/z 406.1 [M+H]$^+$.

(e) 2-(4-Bromobenzyl)-7,8-dihydro-5,7,7-trimethyl-[2H]-imidazo-[1,2-a]pyrazolo[4,3-e]pyrimidin-4(5H)-one Thionyl chloride (67 mL, 922 mmol) is added dropwise to a solution of 6-(1-hydroxy-2-methylpropan-2-ylamino)-5-methyl-2-(4-bromobenzyl)-2H-pyrazolo[3,4-d]pyrimidin-4(5H)-one (134 g, 330 mmol) in DMF (800 mL). The reaction mixture is stirred at room temperature until the reaction is complete. The mixture is poured into cold water, and then adjusted to pH 8-9 with ammonium hydroxide aqueous solution. After filtration, the obtained solids are washed with water, and then dried under vacuum to give 118 g of product (yield: 92%). MS (ESI) 388.1 [M+H]$^+$.

(f) 2-(4-Phenoxybenzyl)-7,8-dihydro-5,7,7-trimethyl-[2H]-imidazo-[1,2-a]pyrazolo[4,3-e]pyrimidin-4(5H)-one 2-(4-Bromobenzyl)-7,8-dihydro-5,7,7-trimethyl-[2H]-imidazo-[1,2-a]pyrazolo[4,3-e]pyrimidin-4(5H)-one (118 g, 304 mmol) is added into a suspension of phenol (57 g, 606 mmol) and cesium carbonate (200 g, 614 mmol) in NMP (900 mL), followed by 2,2,6,6-tetramethylheptane-3,5-dione (7 mL, 33.5 mmol) and CuCl (15 g, 152 mmol). The reaction mixture is heated at 120° C. under argon atmosphere for 10 h. After the completion of the reaction, the mixture is diluted with water (4 L), and then extracted with ethyl acetate. The combined organic phase is evaporated to dryness. The obtained crude product is purified by silica gel column chromatography to give 103 g of product (yield: 84%). MS (ESI) m/z 402.2 [M+H]$^+$.

(g) 7,8-Dihydro-5,7,7-trimethyl-[2H]-imidazo-[1,2-a]pyrazolo[4,3-e]pyrimidin-4(5H)-one TFA (600 mL) is added into a suspension of 2-(4-phenoxybenzyl)-7,8-dihydro-5,7,7-trimethyl-[2H]-imidazo-[1,2-a]pyrazolo[4,3-e]pyrimidin-4(5H)-one (103 g, 257 mmol) in methylene chloride (210 mL) to give a tan solution, and then TFMSA (168 mL) is added. The reaction mixture is stirred at room temperature until the starting material disappeared. The mixture is poured into cold water (3 L). After filtration, the filter cake is washed with water twice, and then basified with ammonium hydroxide aqueous solution, followed by adding ethyl acetate with stirring. The precipitated solids are filtered, washed successively with water three times, ethyl acetate twice and methanol once, and then dried under vacuum to give 45 g of product (yield: 80%). MS (ESI) m/z 220.2 [M+H]+.

(h) 7,8-Dihydro-2-(4-methoxyphenyl)-5,7,7-trimethyl-[2H]-imidazo-[1,2-a]pyrazolo[4,3-e]pyrimidin-4(5H)-one A suspension of 7,8-dihydro-5,7,7-trimethyl-[2H]-imidazo-[1,2-a]pyrazolo[4,3-e]pyrimidin-4(5H)-one (3 g, 13.68 mmol), 1-(chloromethyl)-4-methoxybenzene (1.99 mL, 14.37 mmol) and $K_2CO_3$ (3.78 g, 27.37 mmol) in DMF (50 mL) is stirred at room temperature until the reaction is complete. The solvent is removed, and the residue is washed with water three times (3×70 mL), and then dried under vacuum to give 4.3 g of crude product (yield: 93%), which is used in the next step without further purification. MS (ESI) m/z 340.2 [M+H]+.

(i) 7,8-Dihydro-2-(4-methoxyphenyl)-3-chloro-5,7,7-trimethyl-[2H]-imidazo-[1,2-a]pyrazolo[4,3-e]pyrimidin-4(5H)-one 1.0M LiHMDS (20 mL, 20 mmol) in THF is added dropwise into a solution of 7,8-dihydro-2-(4-methoxyphenyl)-5,7,7-trimethyl-[2H]-imidazo-[1,2-a]pyrazolo[4,3-e]pyrimidin-4(5H)-one (4.3 g, 12.67 mmol) and hexachloroethane (3.33 g, 13.94 mmol) in methylene chloride (100 mL) at 25° C. The reaction mixture is stirred at 25° C. for 30 min, and then quenched with water (150 mL). The methylene chloride phase is separated, and the water phase is extracted with methylene chloride twice (2×60 mL). The combined methylene chloride phase is washed with brine three times (3×70 mL) and the methylene chloride is evaporated to dryness to give 4.6 g of crude product (yield: 97%), which is used in the next step without further purification. MS (ESI) m/z 374.1 [M+H]+.

(j) 7,8-Dihydro-3-chloro-5,7,7-trimethyl-[2H]-imidazo-[1,2-a]pyrazolo[4,3-e]pyrimidin-4(5H)-one To a suspension of 7,8-dihydro-2-(4-methoxyphenyl)-3-chloro-5,7,7-trimethyl-[2H]-imidazo-[1,2-a]pyrazolo[4,3-e]pyrimidin-4(5H)-one (4.6 g, 12.31 mmol) in TFA (23 mL) is added TFMSA (1.7 mL) slowly. The reaction mixture is stirred at room temperature overnight. Solvents are removed under reduced pressure. The obtained residue is treated with water (100 mL), and then adjusted to pH 8-9 with 28% ammonium hydroxide (10 mL) at 0° C. After filtration, the filtrate is concentrated to approximately 15 mL, and then extracted with 10% methanol in methylene chloride (5×60 mL). The combined organic phase is evaporated to dryness to give 1.94 g of crude product (yield: 62%), which is used in the next step without further purification. MS (ESI) m/z 254.1 [M+H]+.

(k) 7,8-Dihydro-2-(pyridin-4-yl-methyl)-3-chloro-5,7,7-trimethyl-[2H]-imidazo-[1,2-a]pyrazolo[4,3-e]pyrimidin-4(5H)-one A suspension of 7,8-dihydro-3-chloro-5,7,7-trimethyl-[2H]-imidazo-[1,2-a]pyrazolo[4,3-e]pyrimidin-4(5H)-one (200 mg, 0.788 mmol), 4-chloromethyl pyridine (151 mg, 0.946 mmol) and $K_2CO_3$ (545 mg, 3.94 mmol) in DMF (7 mL) is stirred at 95° C. until the reaction is complete (approximately 2 h). The solvent is removed and the obtained crude product is purified on a 24 g neutral aluminum oxide cartridge, eluted with a gradient of 0 to 100% ethyl acetate in hexanes over 15 minutes, then eluted with ethyl acetate at a flow rate of 25 ml/min for 30 minutes to give 128 mg of product (yield: 47%). MS (ESI) m/z 345.1 [M+H]+.

(l) 7,8-Dihydro-2-(pyridin-4-yl-methyl)-3-(4-fluorophenylamino)-5,7,7-trimethyl-[2H]-imidazo-[1,2-a]pyrazolo[4,3-e]pyrimidin-4(5H)-one A suspension of 7,8-dihydro-2-(pyridin-4-yl-methyl)-3-chloro-5,7,7-trimethyl-[2H]-imidazo-[1,2-a]pyrazolo[4,3-e]pyrimidin-4(5H)-one (120 mg, 0.348 mmol), 4-fluoro-benzenamine (36 μL, 0.383 mmol) and potassium carbonate (96 mg, 0.696 mmol) in tert-amyl alcohol (2.3 mL) is degassed with argon and then Xantphos (8.1 mg, 0.0139 mmol) and $Pd_2(dba)_3$ (6.4 mg, 0.00696 mmol) are added. The suspension is degassed again, and then heated to 110° C. The reaction mixture is stirred at 110° C. under argon for 8 h. After cooling to room temperature, the mixture is filtered. The filtrate is evaporated to dryness under reduced pressure. The obtained residue is treated with DMF and then filtered with a microfilter. The filtrate is purified with a semi-preparative HPLC system using a gradient of 0-20% acetonitrile in water with 0.1% formic acid over 16 minutes to give 84 mg of the final product as a formate salt (HPLC purity: 98%; yield: 52%). 1H NMR (500 MHz, Chloroform-d) δ 8.50 (d, J=5.0 Hz, 2H), 8.18 (s, 1H), 7.26 (s, 1H), 6.97-6.93 (m, 2H), 6.90-6.76 (m, 4H), 4.84 (s, 2H), 3.72 (s, 2H), 3.37 (s, 3H), 1.45 (s, 6H). MS (ESI) m/z 420.2 [M+H]+.

Example 2: 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one

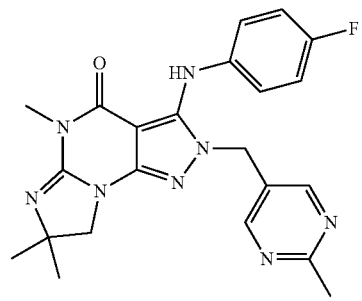 [SMILES: Cc1ncc(Cn2nc3c(c2Nc2ccc(F)cc2)C(=O)N(C)C2=NC(C)(C)CN23)cn1]

(a) 7,8-Dihydro-2-(2-methyl-pyrimidin-5-yl-methyl)-5,7,7-trimethyl-[2H]-imidazo-[1,2-a]pyrazolo[4,3-e]pyrimidin-4(5H)-one A suspension of 7,8-Dihydro-5,7,7-trimethyl-[2H]-imidazo-[1,2-a]pyrazolo[4,3-e]pyrimidin-4(5H)-one (200 mg, 0.92 mmol), 5-(chloromethyl)-2-methylpyrimidine (136 mg, 0.84 mmol) and $K_2CO_3$ (350 mg, 2.56 mmol) in DMF (6 mL) is stirred at room temperature until the reaction is complete. The reaction mixture is filtered, and the filter cake is rinsed with DMF. The collected filtrate is evaporated to dryness to give 242 mg of crude product (crude yield: 78%), which is used in the next step without further purification. MS (ESI) m/z 326.2 [M+H]+.

(b) 7,8-Dihydro-2-(2-methyl-pyrimidin-5-yl-methyl)-3-chloro-5,7,7-trimethyl [2H]-imidazo-[1,2-a]pyrazolo[4,3-e]pyrimidin-4(5H)-one 1.0M LiHMDS (1.14 mL, 1.14 mmol) in THF is added dropwise into a solution of 7,8-dihydro-2-(2-methyl-pyrimidin-5-yl-methyl)-5,7,7-trimethyl-[2H]-imidazo-[1,2-a]pyrazolo[4,3-e]pyrimidin-4(5H)-one (370 mg, 1.14 mmol) and hexachloroethane (807 mg, 3.42 mmol) in methylene chloride (4 mL) at 25° C. The reaction mixture is stirred at room temperature for 30 min, and then diluted with methylene chloride (100 mL). The mixture is washed successively with saturated NaHCO₃ solution (15 mL) and brine (15 mL), and then evaporated to dryness. The obtained crude product is purified on a 24 g basic aluminum oxide cartridge, eluted with ethyl acetate at a flow rate of 25 mL/min to give 402 mg of product (yield: 95%). MS (ESI) m/z 360.1 [M+H]⁺.

(c) 7,8-Dihydro-2-(2-methyl-pyrimidin-5-yl-methyl)-3-(4-fluorophenylamino)-5,7,7-trimethyl-[2H]-imidazo-[1,2-a]pyrazolo[4,3-e]pyrimidin-4(5H)-one A suspension of 7,8-dihydro-2-(2-methyl-pyrimidin-5-yl-methyl)-3-chloro-5,7,7-trimethyl-[2H]-imidazo-[1,2-a]pyrazolo[4,3-e]pyrimidin-4(5H)-one (350 mg, 0.973 mmol), 4-fluorobenzenamine (110 µL, 1.167 mmol) and potassium carbonate (269 mg, 1.946 mmol) in tert-amyl alcohol (3.0 mL) is degassed with argon and then Xantphos (45 mg, 0.0778 mmol) and Pd₂(dba)₃ (36 mg, 0.039 mmol) are added. The suspension is degassed again, and then heated to 110° C. The reaction mixture is stirred at 110° C. under argon for 24 h. After cooling to room temperature, the mixture is filtered. The filtrate is evaporated to dryness under reduced pressure. The obtained residue is treated with DMF and then filtered with a microfilter. The filtrate is purified with a semi-preparative HPLC system using a gradient of 0-20% acetonitrile in water with 0.1% formic acid over 16 minutes to give 356 mg of the final product as a formate salt (HPLC purity: 97%; yield: 74%). 1H NMR (500 MHz, Chloroform-d) δ 8.34 (s, 2H), 7.17 (s, 1H), 7.05-7.01 (m, 2H), 6.97-6.94 (m, 2H), 4.84 (s, 2H), 3.75 (s, 2H), 3.37 (s, 3H), 2.70 (s, 3H), 1.48 (s, 6H). MS (ESI) m/z 435.2 [M+H]⁺.

Example 3: 3-((4-fluorophenyl)amino)-5,7,7-trimethyl-2-(pyridin-3-ylmethyl)-7,8-dihydro-2H-imidazo[1,2-a]pyrazolo[4,3-e]pyrimidin-4(5H)-one

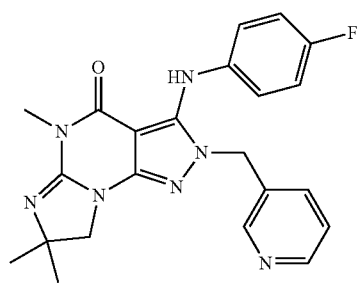 [SMILES: CN1C(=O)c2c(nn(Cc3cccnc3)c2Nc2ccc(F)cc2)N2CC(C)(C)N=C12]

The synthesis method is analogous to Example 2 wherein 3-chloromethyl pyridine is added in step (a) instead of 5-(chloromethyl)-2-methylpyrimidine. The final product is obtained as a formate salt (HPLC purity: 96%; yield: 43%). 1H NMR (500 MHz, Chloroform-d) δ 8.52-8.5 (m, 2H), 8.23 (s, 1H), 7.35 (d, J=5.0 Hz, 1H), 7.22-7.19 (m, 1H), 7.01-6.936.98 (m, 2H), 6.94-6.91 (m, 2H), 4.89 (s, 2H), 3.78 (s, 2H), 3.42 (s, 3H), 1.50 (s, 6H). MS (ESI) m/z 420.2 [M+H]⁺.

Example 4: (6aR,9aS)-2-(4-(6-hydroxypyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4(2H)-one

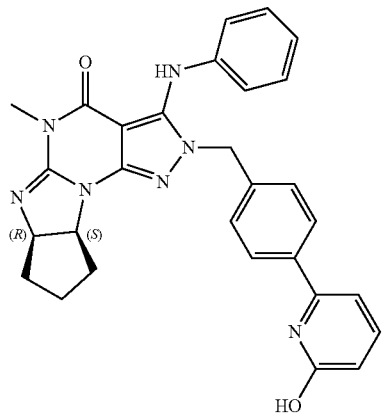

(6aR,9aS)-2-(4-(6-fluoropyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4-(2H)-one (20 mg, 0.039 mmol) is placed in a glass melting point tube and then heated at 240° C. for 90 min. After cooled to room temperature, the material is dissolved in DMF and then purified with a semi-preparative HPLC system using a gradient of 0-24% acetonitrile in water with 0.1% formic acid over 16 minutes to give 12 mg of the title compound as a white solid (HPLC purity: 99%; yield: 60%). ¹H NMR (400 MHz, Chloroform-d) δ 10.47 (s, 1H), 7.49-7.35 (m, 3H), 7.28-7.16 (m, 2H), 7.09-6.97 (m, 3H), 6.95 (s, 1H), 6.87 (d, J=7.9 Hz, 2H), 6.46 (d, J=9.1 Hz, 1H), 6.35 (d, J=6.9 Hz, 1H), 4.89 (s, 2H), 4.78-4.61 (m, 2H), 3.32 (s, 3H), 2.21 (dd, J=12.8, 6.1 Hz, 1H), 2.07-1.90 (m, 1H), 1.86-1.43 (m, 4H). MS (ESI) m/z 506.2 [M+H]⁺.

Example 5: 4-(((6aR,9aS)-5-methyl-4-oxo-3-(phenylamino)-4,5,7,8,9,9a-hexahydrocyclopenta[4,5]imidazo[1,2-a]pyrazolo[4,3-e]pyrimidin-2(6aH)-yl)methyl)benzenesulfonamide

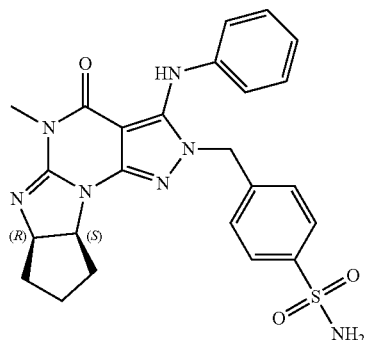

A suspension of (6aR,9aS)-5-methyl-3-(phenylamino)-5,6a,7,8,9,9a-hexahydrocyclopenta[4,5]imidazo[1,2-a]pyrazolo[4,3-e]pyrimidin-4-(2H)-one (100 mg, 0.31 mmol), 4-(bromomethyl)benzenesulfonamide (93 mg, 0.37 mmol) and K₂CO₃ (52 mg, 0.37 mmol) in DMF (3 mL) is stirred at room temperature until the reaction is complete. The reaction mixture is filtered and the collected filtrate is purified with a semi-preparative HPLC system using a gradient of 0-35% acetonitrile in water with 0.1% formic acid over 16 minutes to give the title compound as an off-white solid (33 mg; HPLC purity: 97%; yield: 22%). $^1$H NMR (500 MHz, CDCl₃) δ 7.80 (d, J=8.0 Hz, 2H), 7.32-7.26 (m, 2H), 7.16-7.11 (m, 1H), 7.08 (d, J=8.0 Hz, 2H), 7.02 (s, 1H), 6.93 (d, J=7.9 Hz, 2H), 5.01-4.89 (m, 2H), 4.84 (br, 2H), 4.83-4.76 (m, 2H), 3.37 (s, 3H), 2.28 (dd, J=12.5, 6.1 Hz, 1H), 2.18-1.72 (m, 4H), 1.68-1.55 (m, 1H). MS (ESI) m/z 492.2 [M+H]$^+$.

Example 6: 3-((4-fluorophenyl)amino)-5,7,7-trimethyl-2-((6-methylpyridin-3-yl)methyl)-7,8-dihydro-2H-imidazo[1,2-a]pyrazolo[4,3-e]pyrimidin-4(5H)-one

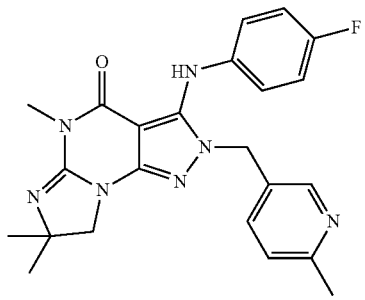 [SMILES: Cc1ccc(Cn2nc3c(c2Nc2ccc(F)cc2)C(=O)N(C)C2=NC(C)(C)CN23)cn1]

(a) 7-(4-methoxybenzyl)-5-methyl-2-((6-methylpyridin-3-yl)methyl)-2H-pyrazolo[3,4-d]pyrimidine-4,6(5H,7H)-dione A suspension of 7-(4-methoxybenzyl)-5-methyl-2H-pyrazolo[3,4-d]pyrimidine-4,6(5H,7H)-dione (6.28 g, 22 mmol), 5-(chloromethyl)-2-methylpyridine (3.1 g, 22 mmol) and K₂CO₃ (15 g, 110 mmol) in DMF (30 mL) and CH₂Cl₂ (30 mL) is stirred at room temperature until the reaction is complete. The reaction mixture is diluted with water (300 mL) and then extracted with CH₂Cl₂ (60 mL×3). The combined organic phase is washed with 5% citric acid (40 mL×3) and brine (40 mL×2), and then evaporated to dryness under reduced pressure to give 9.5 g of product as a pale yellow solid. MS (ESI) m/z 392.2 [M+H]$^+$.

(b) 3-Chloro-7-(4-methoxybenzyl)-5-methyl-2-((6-methylpyridin-3-yl)methyl)-2H-pyrazolo[3,4-d]pyrimidine-4,6(5H,7H)-dione 1.0M LiHMDS (8 mL, 8 mmol) in THF is added dropwise into a solution of 7-(4-methoxybenzyl)-5-methyl-2-((6-methylpyridin-3-yl)methyl)-2H-pyrazolo[3,4-d]pyrimidine-4,6(5H,7H)-dione (783 mg, 2.0 mmol) and hexachloroethane (495 mg, 2.1 mmol) in methylene chloride (5 mL) at room temperature. The reaction mixture is stirred at room temperature for an hour, and then quenched with water (100 mL). The methylene chloride phase is separated, and the water phase is extracted with methylene chloride (20 mL×3). The combined methylene chloride phase is evaporated to dryness. The residue is purified on a silica column using a gradient of 0% to 20% methanol in ethyl acetate to give product (370 mg, 43% yield). MS (ESI) m/z 426.1 [M+H]$^+$.

(c) 3-(4-Fluorophenylamino)-7-(4-methoxybenzyl)-5-methyl-2-((6-methylpyridin-3-yl)methyl)-2H-pyrazolo[3,4-d]pyrimidine-4,6(5H,7H)-dione A suspension of 3-chloro-7-(4-methoxybenzyl)-5-methyl-2-((6-methylpyridin-3-yl)methyl)-2H-pyrazolo[3,4-d]pyrimidine-4,6(5H,7H)-dione (210 mg, 0.49 mmol), 4-fluorobenzenamine (108 mg, 0.97 mmol) and potassium carbonate (202 mg, 1.46 mmol) in tert-amyl alcohol (2.5 mL) is degassed with argon and then Xantphos (14 mg, 0.024 mmol) and Pd₂(dba)₃ (12 mg, 0.013 mmol) are added. The suspension is degassed again, and then heated to 110° C. The reaction mixture is stirred at 110° C. under argon for 24 h. After cooled to room temperature, the mixture is diluted with water (100 mL) and then extracted with CH₂Cl₂(30 mL×3). The combined organic phase is evaporated to dryness under reduced pressure to give 250 mg of crude product, which is used in the next step without further purification. MS (ESI) m/z 501.3 [M+H]$^+$.

(d) 3-(4-Fluorophenylamino)-5-methyl-2-((6-methylpyridin-3-yl)methyl)-2H-pyrazolo[3,4-d]pyrimidine-4,6(5H,7H)-dione TFA (1 mL) is slowly added into a suspension of crude 3-(4-fluorophenylamino)-7-(4-methoxybenzyl)-5-methyl-2-((6-methylpyridin-3-yl)methyl)-2H-pyrazolo[3,4-d]pyrimidine-4,6(5H,7H)-dione (250 mg) in methylene chloride (6 mL), and then TFMSA (0.5 mL) is added slowly. The reaction mixture is stirred at room temperature for an hour. Solvents are removed under reduced pressure. The residue is dissolved in CH₂Cl₂ (10 mL) and then slowly added into a cold saturated NaHCO₃ aqueous solution (30 mL), followed by extraction with CH₂Cl₂ (15 mL×3). The combined organic phase is evaporated to dryness under reduced pressure and further dried on a vacuum pump to give 300 mg of crude product, which is used in the next step without further purification. MS (ESI) m/z 381.1 [M+H]$^+$.

(e) 6-chloro-3-(4-fluorophenylamino)-5-methyl-2-((6-methylpyridin-3-yl)methyl)-2H-pyrazolo[3,4-d]pyrimidin-4(5H)-one Crude 3-(4-fluorophenylamino)-5-methyl-2-((6-methylpyridin-3-yl)methyl)-2H-pyrazolo[3,4-d]pyrimidine-4,6(5H,7H)-dione (180 mg) is suspended in POCl₃(10 mL) and then heated at 180° C. in a microwave reactor for an hour. After the mixture is cooled to room temperature, POCl₃ is removed under reduced pressure. The obtained residue is washed with hexanes and then dissolved in CH₂Cl₂:MeOH (10:1). The solution is washed with saturated NaHCO₃ aqueous solution and then extracted with CH₂Cl₂:MeOH (10:1) three time. The combined organic phase is evaporated to dryness under reduced pressure and then further dried under vacuum to give 120 mg of crude product as a grey solid, which is used in the next step without further purification. MS (ESI) m/z 399.1 [M+H]$^+$.

(f) 3-(4-Fluorophenylamino)-6-(1-hydroxy-2-methylpropan-2-ylamino)-5-methyl-2-((6-methylpyridin-3-yl)methyl)-2H-pyrazolo[3,4-d]pyrimidin-4(5H)-one A mixture of crude 6-chloro-3-(4-fluorophenylamino)-5-methyl-2-((6-methylpyridin-3-yl)methyl)-2H-pyrazolo[3,4- d]pyrimidin-4(5H)-one (120 mg), DIPEA (0.6 mL) and 2-amino-2-methylpropan-1-ol (300 mg, 3.4 mmol) in DMA (10 mL) in a sealed vial is heated at 105° C. for 20 h. After cooled to room temperature, the mixture is diluted with saturated NaHCO$_3$ aqueous solution (100 mL) and then extracted with CH$_2$Cl$_2$ (30 mL×3). The combined organic phase is evaporated to dryness under reduced pressure. The residue is purified with a semi-preparative HPLC system using a gradient of 0-20% acetonitrile in water containing 0.1% formic acid over 16 min to give 26 mg of product. MS (ESI) m/z 452.2 [M+H]$^+$.

(g) 3-((4-Fluorophenyl)amino)-5,7,7-trimethyl-2-((6-methylpyridin-3-yl)methyl)-7,8-dihydro-2H-imidazo[1,2-a]pyrazolo[4,3-e]pyrimidin-4(5H)-one Thionyl chloride (two drops) is added dropwise to a solution of 3-(4-fluorophenylamino)-6-(1-hydroxy-2-methylpropan-2-ylamino)-5-methyl-2-((6-methylpyridin-3-yl)methyl)-2H-pyrazolo[3,4-d]pyrimidin-4(5H)-one (26 mg, 0.058 mmol) in DMF (0.5 mL) and CH$_2$Cl$_2$ (1 mL). The reaction mixture is stirred at room temperature for 30 min. After the solvents are removed under reduced pressure, the residue is purified with a semi-preparative HPLC system using a gradient of 0-20% acetonitrile in water containing 0.1% formic acid over 16 min to give 13.9 mg of product as an off-white solid (56% yield; HPLC purity: 95%). $^1$H NMR (500 MHz, Chloroform-d) δ 8.12 (s, 1H), 7.29-7.25 (m, 1H), 7.06 (d, J=7.9 Hz, 1H), 7.00 (t, J=8.4 Hz, 2H), 6.97-6.89 (m, 2H), 4.83 (s, 2H), 3.74 (s, 2H), 3.37 (s, 3H), 2.52 (s, 3H), 1.47 (s, 6H). MS (ESI) m/z 434.2 [M+H]$^+$.

Example 7: 4-((3-((4-fluorophenyl)amino)-5,7,7-trimethyl-4-oxo-4,5,7,8-tetrahydro-2H-imidazo[1,2-a]pyrazolo[4,3-e]pyrimidin-2-yl)methyl)benzenesulfonamide

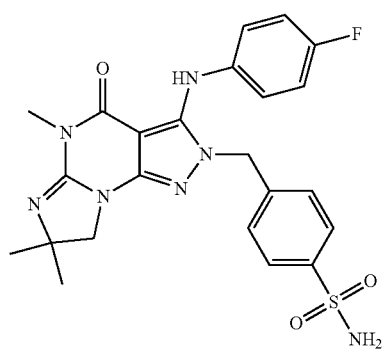 [SMILES: CN1C(=O)c2c(nn(Cc3ccc(S(N)(=O)=O)cc3)c2Nc2ccc(F)cc2)N2CC(C)(C)N=C12]

A suspension of 3-((4-fluorophenyl)amino)-5,7,7-trimethyl-7,8-dihydro-2H-imidazo[1,2-a]pyrazolo[4,3-e]pyrimidin-4(5H)-one (132 mg, 0.50 mmol), 4-(bromomethyl)benzenesulfonamide (101 mg, 0.40 mmol) and Na$_2$CO$_3$ (43 mg, 0.41 mmol) in DMF (4 mL) is stirred at room temperature overnight. The reaction mixture is filtered and the collected filtrate is purified with a semi-preparative HPLC system using a gradient of 0-20% acetonitrile in water with 1% formic acid over 16 minutes to give the title compound as an off-white solid (8.8 mg; HPLC purity: 97%). $^1$H NMR (500 MHz, Chloroform-d) δ 7.81 (d, J=8.2 Hz, 2H), 7.09 (d, J=8.2 Hz, 2H), 6.97 (t, J=8.4 Hz, 2H), 6.93-6.86 (m, 3H), 4.88 (s, 2H), 4.79 (br, 2H), 3.71 (s, 2H), 3.36 (s, 3H), 1.43 (s, 6H). MS (ESI) m/z 498.1 [M+H]$^+$.

Example 8: 3-((4-fluorophenyl)amino)-2-(4-(6-hydroxypyridin-2-yl)benzyl)-5,7,7-trimethyl-7,8-dihydro-2H-imidazo[1,2-a]pyrazolo[4,3-e]pyrimidin-4(5H)-one

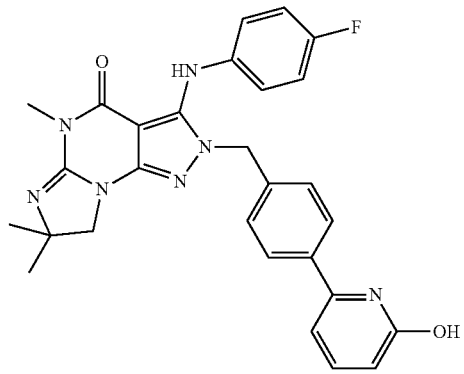 [SMILES: CN1C(=O)c2c(nn(Cc3ccc(-c4cccc(O)n4)cc3)c2Nc2ccc(F)cc2)N2CC(C)(C)N=C12]

3-((4-fluorophenyl)amino)-2-(4-(6-fluoropyridin-2-yl)benzyl)-5,7,7-trimethyl-7,8-dihydro-2H-imidazo[1,2-a]pyrazolo[4,3-e]pyrimidin-4(5H)-one (350 mg, 0.68 mmol) is suspended in water (3 mL), followed by adding concentrated HCl (3 mL) and dioxane (6 mL). The mixture is heated at reflux for 24 h. After the solvents are removed under reduced pressure, the residue is purified with a semi-preparative HPLC system using a gradient of 0-22% acetonitrile in water with 1% formic acid over 16 minutes to give 240 mg of the title compound as an off-white solid (HPLC purity: 95%; yield: 69%). $^1$H NMR (400 MHz, Chloroform-d) δ 7.59-7.46 (m, 3H), 7.10 (d, J=8.3 Hz, 2H), 7.02-6.85 (m, 4H), 6.55 (dd, J=9.1, 1.0 Hz, 1H), 6.47 (dd, J=7.0, 1.0 Hz, 1H), 4.96 (s, 2H), 3.79 (s, 2H), 3.37 (s, 3H), 1.50 (s, 6H). MS (ESI) m/z 512.2 [M+H]$^+$.

Example 9: 2-(4-(6-hydroxypyridin-2-yl)benzyl)-3,5,7,7-tetramethyl-7,8-dihydro-2H-imidazo[1,2-a]pyrazolo[4,3-e]pyrimidin-4(5H)-one

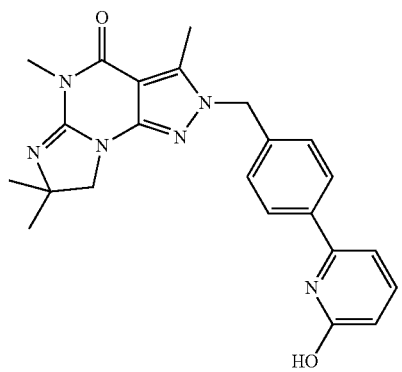 [SMILES: Cc1c2c(nn1Cc1ccc(-c3cccc(O)n3)cc1)N1CC(C)(C)N=C1N(C)C2=O]

The synthesis method is analogous to Example 8 wherein 2-(4-(6-fluoropyridin-2-yl)benzyl)-3,5,7,7-tetramethyl-7,8-dihydro-2H-imidazo[1,2-a]pyrazolo[4,3-e]pyrimidin-4(5H)-one is used as the starting material instead of 3-((4- fluorophenyl)amino)-2-(4-(6-fluoropyridin-2-yl)benzyl)-5,7,7-trimethyl-7,8-dihydro-2H-imidazo[1,2-a]pyrazolo[4,3-e]pyrimidin-4(5H)-one. Final product is obtained as a white solid (HPLC purity: 98%; yield: 65%). $^1$H NMR (500 MHz, Chloroform-d) δ 8.13 (s, 1H), 7.65 (d, J=8.3 Hz, 2H), 7.57 (dd, J=9.1, 7.0 Hz, 1H), 7.29 (d, J=8.3 Hz, 2H), 6.61 (dd, J=9.2, 1.0 Hz, 1H), 6.56 (dd, J=7.1, 1.0 Hz, 1H), 5.28 (s, 2H), 3.82 (s, 2H), 3.50 (s, 3H), 2.57 (s, 3H), 1.51 (s, 6H). MS (ESI) m/z 417 [M+H]$^+$.

Example 10: 3-ethyl-2-(4-(6-hydroxypyridin-2-yl)benzyl)-5,7,7-trimethyl-7,8-dihydro-2H-imidazo[1,2-a]pyrazolo[4,3-e]pyrimidin-4(5H)-one

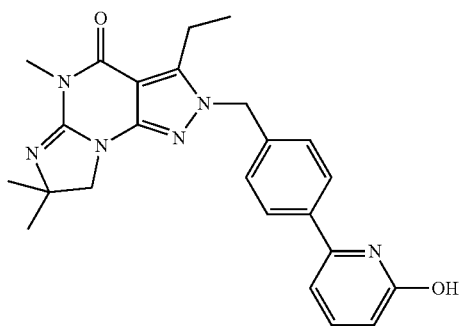 [SMILES: CCc1c2c(nn1Cc1ccc(-c3cccc(O)n3)cc1)N1CC(C)(C)N=C1N(C)C2=O]

A solution of 3-ethyl-2-(4-(6-fluoropyridin-2-yl)benzyl)-5,7,7-trimethyl-7,8-dihydro-2H-imidazo[1,2-a]pyrazolo[4,3-e]pyrimidin-4(5H)-one (865 mg, 2.0 mmol) in 1N HCl (3 mL) in a sealed microwave vial is heated in a microwave reactor at 100° C. for an hour. After cooled to room temperature, the mixture is neutralized to pH 5-6 with 1N NaOH, diluted with 9 mL of DMF, and then filtered. The filtrate is purified with a semipreparative HPLC system using a gradient of 0-19% acetonitrile in water with 1% formic acid over 16 minutes to give 150 mg of the title compound as an off-white solid (HPLC purity: 99%; yield: 17%). MS (ESI) m/z 431 [M+H]$^+$.

Example 11: Measurement of PDEI Inhibition In Vitro Using IMAP Phosphodiesterase Assay Kit Phosphodiesterase 1 (including PDE1A, PDE1B and PDE1C) is a calcium/calmodulin dependent phosphodiesterase enzyme that converts cyclic guanosine monophosphate (cGMP) to 5'-guanosine monophosphate (5'-GMP). PDEIB can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: Phosphodiesterase enzymes that may be used include: 3',5'-cyclic-nucleotide-specific bovine brain phosphodiesterase (Sigma, St. Louis, Mo.) (predominantly PDEIB but also contains PDE1A and PDE1C) and recombinant full length human PDE1A, PDE1B and PDE1C which may be produced e.g., in HEK or SF9 cells by one skilled in the art. The PDE1 enzyme is reconstituted with 50% glycerol to 2.5 U/ml. One unit of enzyme will hydrolyze 1.0 μmol of 3',5'-cAMP to 5'-AMP per min at pH 7.5 at 30° C. One part enzyme is added to 1999 parts reaction buffer (30 μM CaCl$_2$, 10 U/ml of calmodulin (Sigma P2277), 10 mM Tris-HCl pH 7.2, 10 mM MgCl$_2$, 0.1% BSA, 0.05% NaN$_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature. The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. IC$_{50}$ values are determined by measuring enzyme activity in the presence of 8 to 16 concentrations of compound ranging from 0.0037 nM to 80,000 nM and then plotting drug concentration versus Δmp, which allows IC$_{50}$ values to be estimated using nonlinear regression software (XLFit; IDBS, Cambridge, Mass.).

The Compounds of the Invention are tested in an assay as described or similarly described herein for PDE1 inhibitory activity, which compounds generally have IC$_{50}$ values against bovine PDE1 of less than 75 nM and/or PDE1B (HEK/Sf9) of less than 10 nM and/or PDE1A (HEK) and/or PDE1C (HEK) of less than 1 nM.

Example 12: Pharmacokinetic Analysis of the Compounds of the Invention

Animals: Male, C57BL/6 mice (Jackson Labs, 25-30 g in body weight) are provided by Jackson Laboratories. Up to five mice are housed per cage and are maintained under a 12 hour light/dark cycle with access to food and water ad libitum. All procedures for the handling and use of animals follow the guidelines of the Institutional Animal Care and Use Committee (IACUC) of Columbia University, in accordance with NIH guidelines. Eight week-old mice (N=3/dose level or treatment group) are used in the experiments.

Experimental Treatment: Compounds: Selected Compounds of the Invention are evaluated in the present study. Formulation/Vehicle: 3% 1N HCl, 5% Labrasol and 92% of 5% TPGS in 0.05M Citrate buffer (CB, pH 4.0). The test compound(s) are prepared as solution in vehicle and are dosed in a volume of 8 ml/kg.

Compound Preparation: Powdered stocks of the test compound(s) are measured and dissolved in 3% 1N HCl, 5% Labrasol and 92% of 5% TPGS in 0.05M Citrate buffer (CB, pH 4.0). Two or three layers of 3 mm glass beads are added to the bottom of the 10 ml glass tube to promote mixing. The tube is mixed using a benchtop vortex mixer then sonicated using a VWR sonicator (model 750) for about 5 min until the drug powder is totally dissolved in into a vehicle solution.

Treatment of Animals: Mice (N=3 mice/dose/time point) receive a 10 mg/kg oral (PO) dose of the test compound(s) at time 0. Groups of mice are killed at a specified time point, either 0.25, 0.5, 1, or 2 h after drug administration. Brain tissue is collected and frozen at −80° C., until analysis. Blood is collected from the mice by puncture of the retro-orbital vein using a Pasteur pipette (VWR, Cat#53283-911), then deposited into silicon-coated blood collection tubes containing 0.105M sodium citrate solution (BD Vacutainer, #366392, Franklin Lakes, N.J.). Blood samples are centrifuged at the speed of 8000 g for 40 minutes in 4° C. (TOMY, refrigerated benchtop microcentrifuge, Fremont, Calif. 94583) and plasma decanted into Eppendorf tubes and frozen at −80° C. until analysis. Plasma and brain tissue samples are processed and analyzed by the analytical group using LC-MS/MS methods, as described below.

Sample Preparation: Samples of plasma are prepared for analysis as follows: 50 μL of the plasma samples is transferred into a 500 al polypropylene microtube (Eppendorf Cat#022363611) as follows:

| Standards | Samples |
| --- | --- |
| 50 μL control (blank) plasma | 50 μL test sample plasma |
| 10 μL standard working solution in 1:1 Methanol:Water | 10 μL 1:1 Methanol:Water |
| 150 μL 0.1 μM Standard in Methanol | 150 μL 0.1 μM Standard in Methanol |

Each tube is vortex mixed, then centrifuged for 20 min at 15000 rpm. The supernatant is collected and 100 μL of each is then transferred into a 96-well polypropylene Elisa plate for mass spectrometric analysis.

Samples of brain homogenate were prepared for analysis as follows: Approximately 0.5 g of brain tissue is weighed and homogenized with 1 mL Milli-Q water. Then 60 μL of the resulting homogenate is then transferred into a clean 500 μL polypropylene microtube (Eppendorf Cat#022363611) and treated as shown below:

| Standards | Samples |
| --- | --- |
| 60 μL control (blank) brain homogenate | 60 μL test sample brain homogenate |
| 20 μL standard working solution in 1:1 Methanol:Water | 20 μL 1:1 Methanol:Water |
| 180 μL 0.1 μM Standard in Methanol | 180 μL 0.1 μM Standard in Methanol |

Each tube is vortexed, then centrifuged for 20 min at 15000 rpm using a Tomy benchtop centrifuge at 4° C. Standard is an internal standard used for LC-MS/MS quantitation. 150 μL of each supernatant is then transferred into a 96-well plate for mass spectrometric analysis. Any remaining plasma or homogenate is stored at approximately −20° C. pending any necessary repeat analysis. For each test sample, a calibration curve is prepared covering the range of 0.5-500 ng/mL.

HPLC and Mass Spectrometric Analysis: Analysis to quantify the concentration of each compound in plasma and brain homogenate is carried out using reverse phase HPLC followed by mass spectrometric detection using the parameters listed:

| HPLC: | Waters Alliance 2795 HT |
| --- | --- |
| Mobile phase A: | 0.1% Formic acid in water |
| Mobile phase B: | 0.1% Formic acid in methanol |
| Column: | Phenomenex Synergi 4μ Fusion-RP 50 × 2 mm |
| Column Temperature: | 40° C. |

| Time (min) | Solvent A (%) | Solvent B (%) | Flow Rate (mL/min) |
| --- | --- | --- | --- |
| 0 | 80 | 20 | 0.6 |
| 2 | 0 | 100 | 0.6 |
| 4 | 0 | 100 | 0.6 |

| | |
| --- | --- |
| Waters Alliance 2795 LC rapid equilibration flow (mL/min): | 5 |
| Waters Alliance 2795 LC rapid equilibration time (min): | 0.25 |
| Re-equilibration time (min): | 1 |
| Injection volume (μl): | 10 |

Each compound is detected and quantified using Multiple Reaction Monitoring (MRM) of positive electrospray mode with a Waters QuattroMicro™ mass spectrometry system.

RESULTS: Plasma and Brain Analysis: All the test compound(s) tested could be detected and analyzed when spiked into control plasma. Standard curves are established prior to the analysis of the samples and proved linear over the range of 0.5-1500 ng/mL in plasma and 0.5-500 ng/mL in brain. Plasma and brain levels of each compound are determined and expressed as means±standard deviation for each compound at each time point. Brain and plasma $C_{max}$ and $T_{max}$ values are estimated for each compound by visual inspection of the data. A ratio of brain/plasma concentration (B/P) is also calculated for each compound by dividing Brain $AUC_{(0-2h)}$/Plasma $AUC_{(0-2h)}$ or Brain $C_{max}$/Plasma $C_{max}$.

Results: Using the procedure described or similarly described, the compounds of Examples 2-6 and 8-10 are tested and display excellent oral bioavailability to the plasma with correspondingly low brain exposure (B/P ratios ranging from 0.02-0.33). In particular, the compound of Examples 4-5 and 7-10 have a B/P ratio of less than about 0.05. The compound of Examples 1-3 have a B/P ratio of about 0.1 or less. The compound of Example 6 has a B/P ratio of about 0.3. In contrast, the B/P ratio of (6aR,9aS)-3-(phenylamino)-5,6a,7,8,9,9a-hexahydro-5-methyl-2-(4-(trifluoromethyl)-benzyl)-cyclopent[4,5]imidazo[1,2-a]pyrazolo[4,3-e]pyrimidin-4(2H)-one is about 4.5-4.8.

Example 13: Effects of PDE1 Inhibition on Isoproterenol Induced Cardiac Hypertrophy The compound of Example 2 is tested in a mouse model where the mice are treated with isoproterenol. Such a model can be useful for extrapolating to diseases or disorders involving an enlargement of the heart or cardiac tissue, e.g., congestive heart disease.

Animals: 129S1/SvlmJ mice, 20-40 grams, Jackson Laboratories (Bar Harbor, Me.).

Number and Sex: 40 males.

Housing and Enrichment: Animals are housed individually during the study in shoe-box style cages in an environmentally controlled room.

Food: Animals are provided standard diet food ad libitum.

Water: Animals are provided tap water ad libitum.

Contaminants: There are no known contaminants in the food or water that would interfere with this study.

Environmental Conditions: The animal room temperatures are set to maintain 18 to 24° C. A 12-hour dark cycle are implemented unless interrupted by study procedures.

Animal Selection: Animals are selected for the study based on health status, body weight, or other relevant data as appropriate.

Test Compound of Example 2: Test compound of Example 2 is supplied as a powder. The test article dosing solutions are prepared on the day of administration by dissolving the test compound in the vehicle (0.9% sodium chloride for injection, U.S.P.) at concentration of 2.0 mg/mL stock/dosing solution. The compound are agitated with a vortex mixer and sonicated to ensure the compound is in solution. The 2.0 mg/mL solution is diluted with vehicle to create the 0.2 mg/mL and the 0.6 mg/mL dosing solutions. Dosing solutions are stored in a refrigerator between the daily doses and are allowed to return to room temperature before the evening dose.

Test Compound Isoproterenol: Test compound isoproterenol is supplied by Sigma (St. Louis, Mo.) as a powder. The test article dosing solutions are prepared on the day of administration by dissolving the test compound in the vehicle (0.9% sodium chloride for injection, U.S.P.) at concentration of 2.0 mg/mL. The compound is agitated with a vortex mixer and sonicated to ensure the compound is in solution.

| Test Article | Groups | | | | | |
|---|---|---|---|---|---|---|
| | 1 NA | 2 NA | 3 Vehicle | 4 Example 2 | 5 Example 2 | 6 Example 2 |
| Test Article Concentration (mg/mL) | NA | NA | 0 | 0.2 | 0.6 | 2 |
| Test Article Dosage3 (mg/kg) | NA | NA | 0 | 1 | 3 | 10 |
| Test Article Dose Volume (mL/kg) | NA | NA | 5 | 5 | 5 | 5 |
| Isoproterenol Concentration (mg/mL) | 0 | 2 | 2 | 2 | 2 | 2 |
| Isoproterenol Dosage (mg/kg) | $0^1$ | $10^1$ | $10^2$ | $10^2$ | $10^2$ | $10^2$ |
| Isoproterenol Dose Volume (mL/kg) | 5 | 5 | 5 | 5 | 5 | 5 |
| Number of Male Mice | 6 | 6 | 7 | 7 | 7 | 7 |

Vehicle is 0.9% sodium chloride for injection, U.S.P.
[1]Mice will receive one bolus subcutaneous injection at the listed dose once/day from days 1-13.
[2]Mice will receive one bolus subcutaneous injection at the listed dose once/day from days 4-9.
[3]Mice will receive one bolus intraperitoneal injection at listed dose twice/day from days 1-9.

Mice in group 1 and 2 are dosed daily via subcutaneous administration.

On days 7, 10 and 14, 2 animals from groups 1 and 2 are weighed and then euthanized via CO2 asphyxiation. Hearts are harvested and gently infused with ice cold saline until clear. The entire heart is weighed. The atria are removed and the left ventricle (with septum) is separated from the right ventricle. The ventricles are weighed separately. The left tibia is removed and separated from the soft tissue. Longitudinal measurement are obtained with a digital micrometer.

Mice in groups 3-6 are dosed once/day with isoproterenol subcutaneously from Days 4-9 and twice/day with vehicle or test compound via intraperitoneal administration from Days 1 to 9.

Groups 3-6 Terminal Procedure

On Day 10 (based on the results from Groups 1 and 2) animals from each group are weighed and then euthanized via CO2 asphyxiation. Hearts are harvested and gently infused with ice cold krebs-henseleit buffer (Sigma 3753) until clear. The entire heart is weighed. The atria are removed and the left ventricle (with septum) is separated from the right ventricle. The ventricles are weighed separately. The ventricles are stored in ice cold krebs-henseleit buffer for approximately 15 minutes and then transferred to 10% buffered formalin at room temperature until possible shipment for possible future analysis.

The left tibia is removed and separated from the soft tissue. Longitudinal measurement is obtained with a digital micrometer.

The dissected atria and tibia are disposed of with the rest of the carcass. Prior to cardiectomy, a 0.5 mL sample of blood is withdrawn into a collection tube containing K2-EDTA anticoagulant. The sample is stored on ice until spun in a refrigerated centrifuge. Plasma is separated and frozen on dry ice, and then stored in a freezer set to maintain approximately −20° C. until shipped on dry ice for possible future analysis.

Using the procedure as described or similarly described above, the Compound of Example 2 of the invention is evaluated and provides the following results:

| Group | HW/TL Ratio (mean) | HW/TL Ratio (std error) |
|---|---|---|
| Vehicle | 9.2427 | 0.3364 |
| 1 mg/kg Cmpd 2 | 8.4876 | 0.3507 |
| 3 mg/kg Cmpd 2 | 8.0830 | 0.1489 |
| 10 mg/kg Cmpd 2 | 8.0976 | 0.2279 |

Isoproterenol treatment in mice increases cardiac size (Size is indicated by heart weight (g)/tibia length (mm)) in mice not treated with the compound of Example 2. Oral administration of up to 10 mg/kg results in a statistically significant effect on the development of isoproterenol-induced cardiac hypertrophy. Specifically, at 1 mg/kg, there is about an 8% reduction in the heart weight/tibia length (HW/TL) ratio compared to vehicle, while at both 3 mg/kg and at 10 mg/kg, there is about a 12.5% reduction in HW/TL ratio compared to vehicle. The compound of Example 2 also significantly prevents cardiac hypertrophy at a dose of both 3 mg/kg and 10 mg/kg. Isoproteranol-induced cardiac enlargement, as measured by the (LV+RV)/TL ratio (left ventricle plus right ventricle weight/tibia length), is decreased by 10% compared to vehicle for both 3 mg/kg and 10 mg/kg dosing.

Example 14: Effects of PDE1 Inhibition on Cardiac Hypertrophy in Transverse Aortic Constriction (TAC) Mouse Model Animals: C59Bl/6 mice, 20-40 grams, Charles River (Portage, Mich.).

Number and Sex: 35 males.

Housing and Enrichment: Animals are housed individually during the study in shoe-box style cages in an environmentally controlled room.

Food: Animals are provided standard diet food ad libitum.

Water: Animals are provided tap water ad libitum.

Environmental Conditions: The animal room temperatures are set to maintain 18 to 24° C. A 12-hour dark cycle is implemented unless interrupted by study procedures.

Animal Selection: Animals are selected for the study based on health status, body weight, or other relevant data as appropriate.

Test Compound of Example 2: Test compound of Example 2 is formulated. The test article dosing solutions are prepared by titrating the free base with 1 mole/mole dilute (0.02N) HCl and diluting the dissolved test compound in the vehicle (0.5% methylcellulose in distilled water) to a final concentration of 0.45 mg/mL and 1.5 mg/mL dosing solution. A supply of formulation for thirty days of dosing are prepared (day 1-6 for $1^{st}$ surgical cohort).

Reference Test Compound—Losartan potassium: Losartan is obtained by CorDynamics, and prepared on the day of administration by dissolving in the vehicle (0.5% methylcellulose in distilled water) at concentration of 4.5 mg/mL dosing solution. The compound is agitated with a vortex mixer and sonicated to ensure the compound is in solution.

|  | Groups | | | | |
| --- | --- | --- | --- | --- | --- |
| Test Article | 1 Vehicle | 2 Vehicle | 3 Example 2 | 4 Example 2 | 5 Losartan |
| Test Article Concentration (mg/mL) | NA | 0 | 0.45 | 1.5 | 4.5 |
| Test Article Dosage (mg/kg/dose) | NA | $0^1$ | $3^1$ | $10^1$ | $30^2$ |
| Test Article Dose Volume (mL/kg/dose) | NA | 6.67 | 6.67 | 6.67 | 6.67 |
| Number of Male Mice | 7 | 7 | 7 | 7 | 7 |

Group 1 animals receive sham transverse aortic constriction and Group 2-5 animals receive transverse aortic constriction at day −1.
Vehicle is 0.5% methylcellulose.
[1]Mice receive oral dose as listed above twice/day from day 1 post-surgery until day 28.
[2]Mice receive oral dose as listed above once/day from day 1 post-surgery until day 28

Transverse Aortic Constriction Surgery: Animals are anesthetized with isoflurane using a nose cone connected to a vaporizer that delivers 1-2% isoflurane driven by 100% oxygen. After initial anesthesia with isoflurane, mice receive 1 mg/kg Buprenex SR (1 mg/mL, s.c.) and 10 mg/kg of etomidate (2 mg/mL, i.p.). Animals are intubated for mechanical ventilation. The endotracheal tube is connected to a mechanical ventilator that provides positive-pressure ventilation with 1-2% isoflurane remainder oxygen, set to maintain ~120 breaths/min with a tidal volume of ~200 μL. Body temperature is monitored throughout the experiment.

A sternotomy is performed from the manubrium through the second or third rib in order to expose the aorta in the thoracic cavity. The aorta is cleaned of surrounding tissue and the transverse aorta clamped with a titanium microclip, the diameter similar to a 27 G needle. The transverse aorta from mice in Group 1 is cleaned of surrounding tissue but not clamped. The incision is closed, endotracheal tube is removed and animal is allowed to recover.

Immediately following completion of the surgical procedure, mice is placed in a recovery cage in the recovery room. The animals is returned to general housing once alert and ambulatory.

Length of treatment post-operatively is determined by return to normal pre-operative function. This is judged by attitude, activity level, and appetite. Daily post-op monitoring is performed for 4 days post-op. Stitches are removed when the surgical sites have healed sufficiently, approximately 10-14 days after surgery.

Mice are dosed twice daily with vehicle or the compound of Example 2 via oral administration with approximately 6 hours between each dose beginning at 1 day post-surgery. Mice are dosed once daily with losartan via oral administration. Body weights are taken after arrival, prior to surgery, prior to dosing on the first day of dosing and every third day of dosing for dose calculation purposes.

On day 28, echocardiographic measurements are performed for all experimental groups. Animals are anesthetized with isoflurane using a nose cone connected to a vaporizer that delivers 1-2% isoflurane driven by 100% oxygen. Mice are placed in the dorsal decubitus position on a warming platform to maintain body temperature at 37±0.5° C. Heart rate is monitored throughout the experiment. Transthoracic two-dimensional, B-mode, M-mode and pulsed Doppler images are acquired with a high-resolution echocardiographic system (VeVo 770, Visual Sonics, Toronto, ON, Canada) equipped with a 30-MHz mechanical transducer.

After echocardiographic measurements, animals are euthanized via $CO_2$ asphyxiation. Hearts and lungs are harvested and gently infused with ice cold krebs-henseleit buffer (Sigma 3753) until clear. Lungs are weighed and the right and left lung are separated. The right and left lung are immediately frozen in liquid nitrogen and placed into separate tubes. The entire heart is weighed. The atria are removed and the left ventricle (with septum) is separated from the right ventricle. The ventricles are weighed separately before being divided into two pieces. Ventricle pieces are frozen in liquid nitrogen and placed into separate tubes. Liquid nitrogen samples are stored in a freezer set to maintain approximately −80° C. until shipped on dry ice to the Sponsor for possible future analysis.

The left tibia is removed and separated from the soft tissue. Longitudinal measurement will be obtained with a digital micrometer. The dissected tibia is disposed of with the rest of the carcass.

Prior to cardiectomy, a 0.5 mL sample of blood is withdrawn into a collection tube containing sodium citrate anticoagulant. The sample is stored on ice until spun in a refrigerated centrifuge. Plasma is separated and frozen on dry ice, and then stored in a freezer set to maintain approximately −20° C. until shipped on dry ice for possible future analysis.

Using the procedures described or similarly described above, the following results are obtained:

| Group | Terminal LV + S/TL Ratio (mean) | Terminal LV + S/TL Ratio (std error meas) |
| --- | --- | --- |
| Sham Operation | 4.6 | 0.14 |
| Vehicle | 6.6 | 0.32 |

-continued

| Group | Terminal LV + S/TL Ratio (mean) | Terminal LV + S/TL Ratio (std error meas) |
|---|---|---|
| 3 mg/kg Cmpd 2 | 5.8 | 0.25 |
| 10 mg/kg Cmpd 2 | 5.8 | 0.46 |
| 40 mg/kg Losartan | 6.2 | 0.33 |

The compound of Example 2 at 3 mg/kg and 10 mg/kg shows a tendency to reverse the cardiac hypertrophy induced by the TAC constriction. Hypertrophy is judged based on the heart size (left ventricle+septum weight in mg) normalized to animal size (tibia length in mm), defined as the "TAC ratio". Mice that receive the sham operation show a TAC ratio of 4.6 (mg/mm), while mice that receive the compound of Example 2 at either 3 mg/kg or 10 mg/kg show a TAC ratio of 5.8. In contrast, mice that receive vehicle show a TAC ratio of 6.6, and mice that receive Losartan show a TAC ratio of 6.2. The different between the sham and vehicle TAC groups is statistically significant, while the difference between the sham and compound of Example 2 groups is not statistically significant. The difference between the vehicle group and the Losartan group is also not statistically significant. Thus, the compound of Example 2 shows a tendency to reduce TAC-induced hypertrophy.

What is claimed is:

1. A compound of Formula I:

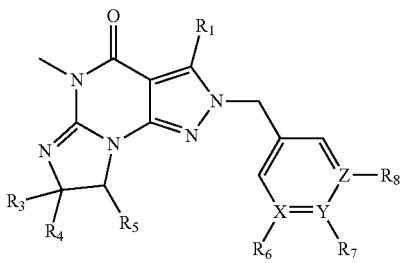

Formula I wherein
(i) $R_1$ is $C_{1-4}$alkyl or —NH($R_2$), wherein $R_2$ is phenyl optionally substituted with halo;
(ii) X, Y and Z are, independently, N or C;
(iii) $R_3$, $R_4$ and $R_5$ are independently H or $C_{1-4}$alkyl; or $R_3$ is H and $R_4$ and $R_5$ together form a tri-methylene bridge;
(iv) $R_6$, $R_7$ and $R_8$ are independently:
H,
$C_{1-4}$alkyl,
pyrid-2-yl substituted with hydroxy, or
—S(O)$_2$—NH$_2$;
(v) Provided that when X, Y and/or Z are N, then $R_6$, $R_7$ and/or $R_8$, respectively, are not present; and when X, Y and Z are all C, then at least one of $R_6$, $R_7$ or $R_8$ is —S(O)$_2$—NH$_2$ or pyrid-2-yl substituted with hydroxy;
in free or salt form.

2. The compound according to claim 1, wherein $R_3$, $R_4$ and $R_5$ are independently H or $C_{1-4}$alkyl, in free or salt form.

3. The compound according to claim 1, wherein $R_3$ and $R_4$ are independently $C_{1-4}$alkyl and $R_5$ is H, in free or salt form.

4. The compound according to claim 1, wherein $R_3$ and $R_4$ are both methyl and $R_5$ is H, in free or salt form.

5. The compound according to claim 1, wherein $R_1$ is —NH($R_2$), wherein $R_2$ is phenyl optionally substituted with halo, in free or salt form.

6. The compound according to claim 1, wherein $R_1$ is —NH($R_2$), wherein $R_2$ is phenyl substituted with halo, in free or salt form.

7. The compound according to claim 1, wherein at least one of X, Y and/or Z is N, the corresponding $R_6$, $R_7$ and/or $R_8$ do not exist, and the remaining $R_6$, $R_7$ and/or $R_8$ are independently H or $C_{1-4}$alkyl, in free or salt form.

8. The compound according to claim 1, wherein X and Z are N and Y is C, in free or salt form.

9. The compound according to claim 8, wherein $R_6$ and $R_8$ do not exist and $R_7$ is $C_{1-4}$alkyl, in free or salt form.

10. The compound according to claim 8, wherein $R_6$ and $R_8$ do not exist and $R_7$ is methyl, in free or salt form.

11. The compound according to claim 1, wherein:
(i) $R_1$ is —NH($R_2$), wherein $R_2$ is phenyl optionally substituted with halo;
(ii) At least one of X, Y and Z is N;
(iii) $R_3$, $R_4$ and $R_5$ are independently H or $C_{1-4}$alkyl; or $R_3$ is H and $R_4$ and $R_5$ together form a tri-methylene bridge,
(iv) $R_6$, $R_7$ and $R_8$ are independently H or $C_{1-4}$alkyl;
(v) Provided that when X, Y and/or Z are N, then $R_6$, $R_7$ and/or $R_8$, respectively, are not present;
in free or salt form.

12. The compound according to claim 11, wherein $R_3$ and $R_4$ are independently $C_{1-4}$alkyl and $R_5$ is H, in free or salt form.

13. The compound according to claim 11, wherein $R_3$ and $R_4$ are both methyl and $R_5$ is H, in free or salt form.

14. The compound according to claim 11, wherein X and Z are N, Y is C and $R_7$ is $C_{1-4}$alkyl, in free or salt form.

15. The compound according to claim 1 selected from the group consisting of:
3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one;
3-((4-fluorophenyl)amino)-5,7,7-trimethyl-2-(pyridin-3-ylmethyl)-7,8-dihydro-2H-imidazo[1,2-a]pyrazolo[4,3-e]pyrimidin-4(5H)-one;
3-((4-fluorophenyl)amino)-5,7,7-trimethyl-2-(pyridin-4-ylmethyl)-7,8-dihydro-2H-imidazo[1,2-a]pyrazolo[4,3-e]pyrimidin-4(5H)-one;
(6aR,9aS)-2-(4-(6-hydroxypyridin-2-yl)benzyl)-5-methyl-3-(phenylamino)-5,6a,7,8,9,9a-hexahydrocyclopenta[4,5]imidazo[1,2-a]pyrazolo[4,3-e]pyrimidin-4(2H)-one;
4-(((6aR,9aS)-5-methyl-4-oxo-3-(phenylamino)-4,5,7,8,9,9a-hexahydrocyclopenta[4,5]imidazo[1,2-a]pyrazolo[4,3-e]pyrimidin-2(6aH)-yl)methyl)benzenesulfonamide;
3-((4-fluorophenyl)amino)-5,7,7-trimethyl-2-((6-methylpyridin-3-yl)methyl)-7,8-dihydro-2H-imidazo[1,2-a]pyrazolo[4,3-e]pyrimidin-4(5H)-one;
4-((3-((4-fluorophenyl)amino)-5,7,7-trimethyl-4-oxo-4,5,7,8-tetrahydro-2H-imidazo[1,2-a]pyrazolo[4,3-e]pyrimidin-2-yl)methyl)benzenesulfonamide;
3-((4-fluorophenyl)amino)-2-(4-(6-hydroxypyridin-2-yl)benzyl)-5,7,7-trimethyl-7,8-dihydro-2H-imidazo[1,2-a]pyrazolo[4,3-e]pyrimidin-4(5H)-one;
2-(4-(6-hydroxypyridin-2-yl)benzyl)-3,5,7,7-tetramethyl-7,8-dihydro-2H-imidazo[1,2-a]pyrazolo[4,3-e]pyrimidin-4(5H)-one;

3-ethyl-2-(4-(6-hydroxypyridin-2-yl)benzyl)-5,7,7-trimethyl-7,8-dihydro-2H-imidazo[1,2-a]pyrazolo[4,3-e]pyrimidin-4(5H)-one;
in free or salt form.

16. The compound according to claim 1 which is the compound 3-((4-fluorophenyl)amino)-5,7,7-trimethyl-2-((2-methylpyrimidin-5-yl)methyl)-7,8-dihydro-2H-imidazo[1,2-a]pyrazolo[4,3-e]pyrimidin-4(5H)-one, in free or salt form.

17. The compound according to claim 1 which is the compound 3-((4-fluorophenyl)amino)-5,7,7-trimethyl-2-(pyridin-3-ylmethyl)-7,8-dihydro-2H-imidazo[1,2-a]pyrazolo[4,3-e]pyrimidin-4(5H)-one, in free or salt form.

18. The compound according to claim 1 which is the compound 3-((4-fluorophenyl)amino)-5,7,7-trimethyl-2-(pyridin-4-ylmethyl)-7,8-dihydro-2H-imidazo[1,2-a]pyrazolo[4,3-e]pyrimidin-4(5H)-one, in free or salt form.

19. A combination comprising the compound according to claim 1, in free or pharmaceutically acceptable salt form, and one or more other therapeutic agents useful for the treatment of cardiovascular disorders, in free or pharmaceutically acceptable salt form.

20. A pharmaceutical composition comprising the compound according to claim 1, in combination or association with a pharmaceutically acceptable diluents or carrier.

21. A method for the treatment of a disease or disorder which may be ameliorated by modulating cGMP/PKG-dependent signaling pathways comprising administering to a patient in need thereof an effective amount of the compound according to claim 1.

22. The method according to claim 21, wherein the disease or disorder is a cardiovascular disorder.

23. The method according to claim 21, wherein the disease or disorder is selected from a group consisting of: hypertrophy, atherosclerosis, myocardial infarction, congestive heart failure, angina, hypertension, essential hypertension, pulmonary hypertension, pulmonary arterial hypertension, secondary pulmonary hypertension, isolated systolic hypertension, hypertension associated with diabetes, hypertension associated with atherosclerosis, renovascular hypertension.

24. The method according to claim 21, wherein the disease or disorder is cardiac hypertrophy.

25. The method according to claim 21, further comprising administering to the patient one or more therapeutic agents selected from an angiotensin II receptor antagonist, angiotensin-converting-enzyme (ACE) inhibitor, neutral endopeptidase (NEP or Neprilvsin) inhibitor, or a PDE5 inhibitor, in free or pharmaceutically acceptable salt form.

26. The method according to claim 21, wherein the disease or disorder is a stroke.

27. The method according to claim 26, wherein the stroke is characterized as a transient ischemic attack.

28. The method according to claim 21, wherein the cardiovascular disease or disorder is associated with a muscular dystrophy.

29. The method according to claim 28, wherein the disease and disorder is a cardiovascular dysfunction which results from a muscular dystrophy selected from the group consisting of: Duchenne muscular dystrophy, Becker muscular dystrophy, limb-girdle muscular dystrophy, myotonic dystrophy, and Emery-Dreifuss muscular dystrophy.

30. The method according to claim 21, wherein the disease or disorder is selected from the group consisting of renal failure, fibrosis, an inflammatory disease or disorder, vascular remodeling and a connective tissue disease or disorder.

31. The combination according to claim 19, wherein the one or more other therapeutic agents useful for the treatment of cardiovascular disorders are selected from the group consisting of an angiotensin II receptor antagonist, a neutral endopeptidase (NEP or Neprilysin) inhibitor and/or a phosphodiesterase 5 (PDE5) inhibitor), in free or pharmaceutically acceptable salt form.

32. The combination according to claim 31, wherein the one or more other therapeutic agents useful for the treatment of cardiovascular disorders are selected from the group consisting of azilsartan, candesartan, eprosartan, irbesartan, losartan, olmesartan, olmesartan medoxomil, saralasin, telmisartan, valsartan, captopril, enalapril, lisinopril, benazapril, ramipril, quinapril, perindopril, imidapril, trandolapril, cilazapril, avanafil, lodenafil, mirodenafil, tadalafil, vardenafil, udenafil, zaprinast, candoxatril, candoxatrilat, omapatrilat, gempatrilat, sampatrilat, AHU-377 and LBQ-657.

33. A pharmaceutical composition comprising the combination according to claim 31, in combination or association with a pharmaceutically acceptable diluents or carrier.

34. A pharmaceutical composition comprising the combination according to claim 32, in combination or association with a pharmaceutically acceptable diluents or carrier.

35. The method according to claim 25, wherein the one or more therapeutic agents comprises an angiotensin II receptor antagonist in free or pharmaceutically acceptable salt form, selected from azilsartan, candesartan, eprosartan, irbesartan, losartan, olmesartan, olmesartan medoxomil, saralasin, telmisartan, and valsartan.

36. The method according to claim 25, wherein the one or more therapeutic agents comprises an angiotensin-converting-enzyme (ACE) inhibitor, in free or pharmaceutically acceptable salt form, selected from captopril, enalapril, lisinopril, benazapril, ramipril, quinapril, perindopril, imidapril, trandolapril, and cilazapril.

37. The method according to claim 25, wherein the one or more therapeutic agents comprises a neutral endopeptidase (NEP or Neprilysin) inhibitor, in free or pharmaceutically acceptable salt form, selected from candoxatril, candoxatrilat, omapatrilat, gempatrilat, sampatrilat, AHU-377 and LBQ-657.

38. The method according to claim 25, wherein the one or more therapeutic agents comprises a PDE5 inhibitor, in free or pharmaceutically acceptable salt form, selected from avanafil, lodenafil, mirodenafil, tadalafil, vardenafil, udenafil, and zaprinast.

* * * * *